United States Patent [19]
Berka et al.

[11] Patent Number: 5,821,102
[45] Date of Patent: Oct. 13, 1998

[54] NUCLEIC ACIDS ENCODING POLYEPTIDES HAVING ABSIDIA LIPASE ACTIVITY

[75] Inventors: Randy M. Berka; Karuppan Chettiar Boominathan, both of Davis, Calif.; Thomas Sandal, Copenhagen N., Denmark

[73] Assignees: Novo Nordisk Biotech Inc., Davis, Calif.; Novo Nordisk A/S, Bassvaerd, Denmark

[21] Appl. No.: 784,651

[22] Filed: Jan. 21, 1997

[51] Int. Cl.⁶ .......................... C12N 15/55; C12N 15/63; C12N 9/20; C12N 1/15

[52] U.S. Cl. .................. 435/198; 536/23.2; 536/23.1; 435/252.3; 435/252.31; 435/252.34; 435/252.35; 435/254.1; 435/254.11; 435/254.2; 435/254.21; 435/254.22; 435/254.23; 435/254.3; 435/254.4; 435/254.6; 435/254.7; 435/254.8; 435/320.1

[58] Field of Search ................... 536/23.1, 23.2; 435/198, 320.1, 252.3, 253.31, 252.34, 252.35, 254.1, 254.3, 254.11, 254.7, 254.4, 254.5, 254.6, 254.8, 254.2, 254.21, 254.22, 254.23

[56] References Cited

U.S. PATENT DOCUMENTS 3,634,195  1/1972  Melachouris ........................ 195/62

FOREIGN PATENT DOCUMENTS

| 0238023 A2 | 9/1987 | European Pat. Off. . |
|---|---|---|
| 0385401 | 9/1990 | European Pat. Off. . |
| 0489718 A1 | 6/1992 | European Pat. Off. . |
| WO 8700859 A1 | 2/1987 | WIPO . |
| WO 9401541 A1 | 1/1994 | WIPO . |
| WO 9414940 A1 | 7/1994 | WIPO . |

OTHER PUBLICATIONS

EMBL, Genbank, DDBJ, Accession No. A34959 (Sep. 1990).
Satyanarayana, T., et al., Chemical Abstracts, vol. 95, No. 13, p. 344 (1981) Abstract No. 111511y.
Dialog Information Services, file 351, Derwent WPI, Dialog accession No. 008384112, WPI accession No. 90–271113/36. (Jul. 1990).
Koritala, S., et al., JAOCS, vol. 64, No. 4, pp. 509–513, (1987).
Aisaka, K., et al., Agric. Biol. Chem., vol. 43, No. 10, pp. 2125–2129 (1979).
Schipper, M.A.A., Persoonia, vol. 14, Part 2, pp. 133–118, (1990).

*Primary Examiner*—Rebecca E. Prouty
*Attorney, Agent, or Firm*—Steve T. Zelson; Cheryl Agris

[57] ABSTRACT

The present invention relates to isolated nucleic acid sequences encoding polypeptides having *Absidia* lipase activity. The invention also relates to nucleic acid constructs, vectors, and host cells comprising the nucleic acid sequences as well as methods for producing the polypeptides. The invention further relates to compositions comprising the polypeptides.

40 Claims, 23 Drawing Sheets

```
GAATTCTAATATAGGCACGCTTTCCCATATAGTGGTTATACCGACCCCAGGATTCATGTAGCATGTGTTTCACTTGCCATTGTCAATGGAA       90

TGTTTATATTCCTTCATAATCCGTCTGCTCGGTGATGCATGCACGTTTGATGTACCACAGATTATGTCAGACAAAAATGTGGAGCAGCAATG      180

AATAGCAAACCATTGACCAAAAAGAGCAATTACTATGCACATTAGCATGAGCGTGGTGCATATCCTGCATTTCCCACGCACAAGAGA           270

GATCTTTATTTTCCTTGTTACACGCACTTTTGAAGCTATTGACTCTCCGTTGGTTCGCGAGAACGGATGTTGAGATATCTCGAGAGTG          360

AGAGAAAGAGAGTTGGGGGCAAAGCCAAGCGCTGATGTGAAAAAGGGACCGATCGTCATCGTTCATTCCTAGCTCTATAAAAAGGTAGCTC       450

TAATCCTTGTCGGCAAAAGCTGCTGTGTCTTGACAAACGATGCGTTTTATTCAGTAGTCATTGCTAGCCGTATCCATCTGCACGTA            540
                                        M  R  F  Y  S  V  V  S  L  L  A  V  S  I  C  T  Y

TGGTGTATCGGGTGTGCCGGTGCCGGTGCAAATTGGTCCACGCGACAAGAGCTATGTCCCTGAACAATATCCTCGAAATGAATGGTCCTTTGCC    630
 G  V  S  G  V  P  V  Q  I  G  P  R  D  X  S  Y  V  P  E  Q  Y  P  P  L  K  M  N  G  P  L  P

TGAAGGTGTAAGGGTCATCCAGGGTTATTGTGAAAACTGTACCATGTATCCCGAAGAAAACAGGTAACTGCACTCTCATCGTCCAAACA         720
 E  G  V  S  V  I  Q  G  Y  C  E  N  C  T  M  Y  P  E  E  N  S  V  T  A  L  S  S  S  K  Q

AGATTACCGTACAGCAAGCGGAGACTGAGATCCAGGCACATACATTTTACACAGGTTGTCAGCCAATGCATATTGCAGAAATGTGATCCC        810
 D  Y  R  I  A  S  E  I  E  L  Q  A  H  I  F  Y  T  A  L  S  A  N  A  Y  C  R  N  V  I  P

TGGTGGCTCCTTGGAGCTGCCCTCACTGCGGATGTCACATCCAAGACTTTAGCACGTTAATCACTGATACCAACGT                      900
 G  G  R  W  S  C  P  H  C  D  V  T  S  N  L  K  I  T  K  T  F  S  T  L  I  T  D  T  N  V
```

FIG.3A

```
CGCTGTGCTGTGTGGCGAAAAGGAGAAGACCATCTATATTGTTTCCCTGCTACAAACTCAATTCCCAACGCCATTGCCGTAGGTTATTA    990
 A  V  A  V  G  E  K  E  K  T  I  Y  I  V  F  R  G  T  N  S  I  R  N  A  I  A

ACCCCAACAACAAGTATACTACTTGGCTTGTCAGCCTTCGCTCATCATATACATTGTCATTTTTATATAGGATATTGTCTTTGTACCAG   1080
                                                                 D  I  V  F  V  P

TGGATTATCCACCTGTTGATGGGCCAAAGTACACAAAAGTATGTGCTAATCACCTGTCATGTCATTAAATAATGCTCAACAAGTTGGTT   1170
 V  D  Y  P  P  V  D  G  A  K  V  H  K

GTTTATTACACAGGATTCCTTGATAGCTATAATGAGGTCCAAGATCAACTTGTAGCCGAGGTCAAAAAACAGCTTGATAACCATCCAGGA   1260
         G  F  L  D  S  Y  N  E  V  Q  D  Q  L  V  A  E  V  K  K  Q  L  Q  N  H  P  G

TACAAGATCGTTGTCGCTGGGTAAACGATTGAAAACGCGGACACTGCACCACCAATATTGAAATCTATACTCAAGGCCAGCCTCGTGGGAA   1350
 Y  K  I  V  V  A  G                                               H  S  L  G

GTGCAACAGCCGTTCTTTGTGCACTTGACCTTTATCACCATGGCCACCACCAATATTGAAATCTATACTCAAGGCCAGCCTCGTGGGAA   1440
 G  A  T  A  V  L  C  A  L  D  L  Y  H  H  G  H  H  N  I  E  I  Y  T  Q  G  Q  P  R  V  G

CACCTGCATTGCAAAGTATGTGATTGGCACAAAGATTCCATACCAAGCTCTGTCAATGAGCGAGACAGTAAGTGCATTGCCGACGACAT   1530
 T  P  A  F  A  K  Y  V  I  G  T  K  I  P  Y  Q  R  L  V  N  E  R  Q

GTCTTTTTCTCGCCGCCCTACTAAGTTTCTATGTATAGTCGTTCCTCCACCTTCCACCTGTGCTTTGGTTCCTACATGCCGGCCGAA   1620
                         V  P  H  L  P  P  G  A  F  G  F  L  H  A  G  E
```

FIG.3B

```
GAGTTTTGGATTATGAAAGACAGCTCGTTGCCTAAGTAGTGTTGTTGCTTGGAAACGCTGAATATGGAATACTCATTGCATGATATATTG  1710
 E  F  W  I  M  K  D  S  S  L

AATAGGCGTATGTCCTAATGGCATTGAGACGGACGACTGCAGCAACTCCATTGTTCCTTTCACCAGTGTCATTGATCATTTAAGGTGAGT  1800
      R  V  C  P  N  G  I  E  T  D  Q  C  S  N  S  I  V  P  F  T  S  V  I  D  H  L  S

AGATTGTCTATATGAGATGATCGTTTACACAATTAACATGTTTGGTCGGTCGAATATAGCTATCTTGACATGAACACTGGTCTTTGTTT  1890
                                                        Y  L  D  M  N  T  G  L  C  L

ATAACCCATTCCTCTCTTAATGTAACCATGTAAATCGTAAATATCCCTCATCCTTCAATATAACAGAGCTATTAACATACTTTGTACAAAACC  1980

AATCCAATGGCTTTTATTACGTGATGATGAATAACCAAGAGTAATTAACGAGTTTAGTCGAAAAGACCGAAGCCCATATCCCTCATCAGAT  2070

TCCTCAGGCTCTTCTTCCTTGGCTTCTTCTCTCTTCCGGCTTCTTCTCTTCACCGGCAGCGGGAGCGGCAGCAGCAACGACGAAAGCATCAGGGTTCTCC  2160

AAGAATTC  2168
```

FIG.3C

```
GAATTCTAATATAAGCACACTTTCCTATATGGCCATTAAACCGACACAGCATTCATAGCCATGGTTCCACTTGGTCAATGTCAATGGAATG   90
TTTATACTTCTTTGATTAGTTAATCGTGATCGTGTTGCATGCACAATTGATGTGTCACAGATTATGTCAGACAAATGTGAAGCAGCAAT   180
TAATAGCAAACCTTTCACCAAAGAGAACAATTACTATGCACATTAGCATGAGTGTGCATATAATGCATTTTCCCACCGCACAAGAGCG   270
AGATCTTTATTTTCCTTGTTACACGCCACTTGGTAGCTATTGACTCTCGTTGGTTCCGGAGAACGGATGAGATATTGAGAGAGTTGG   360
GGGCAAAGCGGAAGCTGATGTGGAAAAAGGGACCGATCACCACCATCTGTCGTTCTTGGCCTCTATATTGCTGTTAGCAGTATTCATCTCCACATCTAGTGTACTGGG   450
                                                                                            M  H  S  Y  I  L  V  L  L  L  A  V  F  I  C  T  S  S  V  L  G
AAAGTGGCTGTGTCTTGACAAGCAATAATGCACTCTTATATTCTAGTATTGCTGTTAGCAGTATTCATCTCCACATCTAGTGTACTGGG   540
  M  H  S  Y  I  L  V  L  L  L  A  V  F  I  C  T  S  S  V  L  G
TGTGCCAATGCAAATTGACCAGCGCGACAAGAAGAGCTATGTCCTGAACAATATCCTGAAAATGAACGGTCCTTGCCTGAAGGTGT   630
 V  P  M  Q  I  D  Q  R  D  K  K  S  Y  V  P  E  Q  Y  P  L  K  M  N  G  P  L  P  E  G  V
AAGCAAAATCCAAGGCTATTGTGAGAACTGTACCATGTATCCTGAAGAAGATAACGTGTCGGCCATTCTCATCATCCAAACAAGACTTCG   720
 S  K  I  Q  G  Y  C  E  N  C  T  M  Y  P  E  E  D  N  V  S  A  F  S  S  S  K  Q  D  F  R
TACTGCAAGTGAAGCTGAGATCCAGATCACATACATTCTTTACACGGTTGTCAGCCAATGCATATTGCAGAACTGTGGTTCCTGGTCG   810
 T  A  S  E  A  E  I  Q  I  T  H  T  F  F  T  A  L  S  A  N  A  Y  C  R  T  V  V  P  G  G  R
ATGGAGCTGCCCCACTGCGATGTCACATCCCACTTGGAAATCACCAAGATTTTAGCACATTGATCACAGATACCAATGTGTTGTTGC   900
 W  S  C  P  H  C  D  V  T  S  H  L  E  I  T  K  I  F  S  T  L  I  T  D  T  N  V  V  V  A
```

FIG.4A

```
TGTTGGCAAAAAGGAGAAAACCATCTATGTGTGTTTTCCGGTACAAGCTCAATTCGGTACAAGCTCAACGCCATTGCTGTAAGTTAAAAACCCCTTAC    990
  V  G  K  K  E  K  T  I  Y  V  V  F  R  G  T  S  S  I  R  N  A  I  A

AAGCATAACAGTGTCAGCCACTTGCTCATTATATTTATTGTCTATTTCTCATAGGATATCTTTGTTCCAGTGAATTATCCACCTGC           1080
                                        D  I  V  F  P  V  N  Y  P  P  A

TGATGGTGCCAAAGTACACAAAGGTACCTGCTGATCACCGTGCATGTATTTGGAACTCAATAGTCTCGTATGCAGGATTCCTGGATAGCT       1170
  D  G  A  K  V  H  K                                                    G  F  L  D  S

ATAACGAAGTCCAAGATCAACTTGTCGCCGAAGTCAAGGCACACAACTCGGTCGTCATCCAGGATACAAGATCATTGTCACTGGTAACACT      1260
  Y  N  E  V  Q  D  Q  L  V  A  E  V  K  A  Q  L  G  R  H  P  G  Y  K  I  I  V  T  G

TGGAAAAAGAAAGACACGGATGCACGTGACTAAATGTCATTGTAGGCATTCGTTGCGGTGCAACAGCTGTTCTCAGTGCACTTG              1350
                                   H  S  L  G  G  A  T  A  V  L  S  A  L

ATCTTTATCACCATGGTCATCACAATATTGAAATTTACACCCAAGGTCAACCAGTGGTACACCAGCATTGCAAATTATGTGATTG            1440
  D  L  Y  H  H  N  I  E  I  Y  T  Q  G  Q  P  R  V  G  T  P  A  F  A  N  Y  V  I

GCACCAAGATCCCATATCAGCCTCTTGTCAATGAGCCTGACAGTAAGTATCTATGAACAATGGGTTTCCTTGTCGACCCATTAAATGATA       1530
  G  T  K  I  P  Y  Q  R  L  V  N  E  R  D

TATTATGTATGTCCTTCCATCTTCCACCTGGAGCTTTGGTTTCCTACATGCTGGTGAAGAGTTTTGGATCATGAAAGACAACTCAT          1620
  I  V  P  H  L  P  P  G  A  F  G  F  L  H  A  G  E  E  F  W  I  M  K  D  N  S
```

FIG.4B

```
TGCGTAAGTATTGTCATGAGAAAGTTGAATATATGATTACTCATTTATATAAAACATATCAAATAGGGTATGTCCAAATGGTATTGAG   1710
 L                                            R  V  C  P  N  G  I  E

ACTGATGACTGTAGCAATTCCATGTCTCCCTTCACTAGTGTCATTGATCATTTAAGGTACGCCACTTTGATTTATTATATCGATCATTCAT   1800
 T  D  D  C  S  N  S  I  V  P  F  T  S  V  I  D  H  L  S

CCAAGAATTAACATATGGAATCATCTAGCTATCTAGAACACTGGTCTCTGTTATAATATTTAGTATCGTTCTCTCCATTC   1890
                         Y  L  D  M  N  T  G  L  C  L

AATCTAATCTTGTCATACAATCGTAAATATCAATAAAGAAACAGGGTAAAATGAATGTTTGTACAAAACCGATTGAATGGCTTTTATTA   1980

TGAGATGAAGGATAACCAAGTGATATTAACGAGTTTAGTCGAAAAGACCGAAGCCCATATCCTCATCAGATTCCTCAGCTTCTTCTTCCT   2070

TAGCTTCTTCCTTCTTTTCCTCACCACCAGCAACFGGAGCGGCAGCAACAACGAAAGCATCAGGGTTCTCCAAGAATTC   2149
```

FIG.4C

```
GAATTCTAATATAAGCACGCTTGCCTATATGGTGACTATACCGATCCCAGCATTCACAACATGTTTCACTTGCCATTGTCAATGGAAT      90

GTTTATATTTCTTTCATTAGGTAATCGTGATTTGTGATGCATGCAAACTTGATGTATCACAGATTATGTCAGACAAATGTGAGCAGCAA     180

TTAATAGCAAAGCATTCACCAAAAAAGAGCAATTACTATGCACATTGGGTATACTACATTTTTCCCACGCACAAGAGATATCTTTACA     270

CTTTTCCTTGTTACACGCCACTTTGAAGCCATTGACTCTCGTTGGTGCGGAGAACGGATGATGATATATCAAGAGAGTTGGGGCAAA     360

GCCGAAGCTGATGTGAAAAAATTACCGATCGTCATTGTCGTTCTTGACTCTATATAAAAGTAGCTTTGATTTGGTCTGCCAAAGTTAC     450

CGTATTCTTGACAAGTGATGCATTCTCATTTGTAGTCATATTGCTAGCTGTATTCATCTGCACGTGCTCTCTATTGGTCTGCCACTGC     540
                   M  H  S  H  F  V  V  I  L  L  A  V  F  I  C  T  C  S  V  L  G  V  P  L

AAATTGATCCACGAGATGACAAGAGCTATGTCCCTGAACAATATCCTTGAAGGTGAATGGTCCTTGCCTGAAGGTCCTGAACCTGATCC     630
 Q  I  D  P  R  D  D  K  S  Y  V  P  E  Q  Y  P  L  K  V  N  G  P  L  P  E  G  V  S  V  I

AAGGCTATTGTGAAAACTGCACCATGTATCCTGAAGAAAATAGTGTATCGGCCATTCTCATCATCCACACAAGATTATCGTATTCAA     720
 Q  G  Y  C  E  N  C  T  M  Y  P  E  E  N  S  V  S  A  F  S  S  S  S  T  Q  D  Y  R  I  A

GCGAGGCCAGAGATTAAGGCCACACATTTTACACAGCCTTGTCAGCCAATGCATACTGCAGAACTGCATCATTCCTGGTGTCAATGGAGTT     810
 S  E  A  E  I  K  A  H  T  F  Y  T  A  L  S  A  N  A  Y  C  R  I  V  I  P  G  G  Q  W  S

GTCCTCACTGTGATGTTGCACCCAACTTGAATATTACCAAGACTTTCACCACCTTGATCACTGATACTAATGTCTTGGTGGCTGTTGGCCG     900
 C  P  H  C  D  V  A  P  N  L  N  I  T  K  T  F  T  T  L  I  T  D  T  N  V  L  V  A  V  G
```

FIG. 5A

```
AAAATGAAAAGACCATCTATGTAGTTTTCGTGGTACAAGCTCAATTCGCAACGCCATTGCTGTAAGTTCACCCCTTACAAACATGACAT        990
 E  N  E  K  T  I  Y  V  V  F  R  G  T  S  I  R  N  A  I  A

TTTATTGCTCATCCAGCTCATTCTTTCTCAGGACATTGTTTTTGTACCAGTGAATTATCCACCTGTTAATGGAGCCAAAGTACACAAA       1080
                         D  I  V  F  V  P  V  N  Y  P  P  V  N  G  A  K  V  H  K

GGTATGTGATCACGTGGTGTCATTTATGTATAAGAATGCTCAATATGCTCATTTACTATCTAGGATTTCTTGATAGCTATAACGAAGTCC    1170
                                                              G  F  L  D  S  Y  N  E  V

AGGATAAACTTGTTGCTGAAGTCAAGGCACAACTTGATCGTCATCCAGGATACAAGATCGTCGTCACTGGGTAAATACCTGAAAAGACAT    1260
 Q  D  K  L  V  A  E  V  K  A  Q  L  D  R  H  P  G  Y  K  I  V  V  T  G

GGATGGCACGTGACTAAATCTGTGTCATTTGTAGACATTCGTTGGGAGGTGCAACAGTCTGTTCTCAGTGCACTTGACCTTTATCACCATG   1350
                              H  S  L  G  G  A  T  A  V  L  S  A  L  D  L  Y  H  H

GCCATGACAATATCGAAATCTATACTCAAGGTCAGCCACCACTGCCAAACTATGTGATTGGCACCAAGATTCCAT                    1440
 G  H  D  N  I  E  I  Y  T  Q  G  Q  P  R  I  G  T  P  E  F  A  N  Y  V  I  G  T  K  I  P

ACCAACGTCTCTGTCAATGAGCGTGACAGTAAGTGTACCTTGCCACAACATGTCGTTTCCCCCGACGTACTAAAGTATTGTATAGTTGTT    1530
 Y  Q  R  L  V  N  E  R  D                                                     I  V

CCTCACCTTCCACCTGGTGCATTGGTTTCCTGCATGCTGGTGAAGAGTTTTGGATCATGAAAGATAGCTCGTTGCCTAAGTAGTGTCAT     1620
 P  H  L  P  P  G  A  F  G  F  L  H  A  G  E  E  F  W  I  M  K  D  S  S  L
```

FIG.5B

```
TGAAAAGGTTGAAGCTATAATACTGACTATATTGGGTAGGCGTATGTCCAAATGGCATTGAAACCGACAACTGCAGCAACTCCATTGTTC    1710
                              R  V  C  P  N  G  I  E  T  D  N  C  S  N  S  I  V

CCTTCACTACTGTCATTGATCATTTAAGGTGAATAGTAGCTTTATTCATGTCATTCATCCATGTAAACTAACACTTGTCTATCTAGCTA    1800
 P  F  T  S  V  I  D  H  L  S                                                         Y

TCTTGACATGAACACTGGTCTCTGTCTATAGTCTTTAGTACCATCCACTCCCTCCTCTTTAATCCCTACAGCAGTAGTTTAAAATAAATCA    1890
 L  D  M  N  T  G  L  C  L

CAAGTATACTTTGTACAAAACCAATCAAATGGCTTTTATTAGATGTGAAAAAGGATGACCAAATGCAATTAACGAGTTTAGTCGAAAAGA    1980

CCGAAGCCCATATCTTCATCAGATTCCTCAGGCTCTCTTCTTCCTTGACTTCTTCCTTCTTGTCATCACCAGCAGCGGGAGCAGCAGCA    2070

ACAACCGAAAGCCATCAGGGTTCTCCAAGAATTC    2102
```

FIG.5C

```
GTACGATCATCATTTGTCTTCTGGTTCTATATAAAAGTAGCTCTGATTTGGTCAGCCAAGGTCACTGTGTCTTGACAAGTGATGCA    90
                                                                                M  H
TTCTCATTTGTAGTCTTATTGCTAGCAGTATTCATCTGCCATGTGCTCTGTATCGGGTGTGCCACTGCAAATTGATCCACCGATGACAA   180
 S  H  F  V  V  L  L  A  V  F  I  C  M  C  S  V  S  G  V  P  L  Q  I  D  P  R  D  D  K
GAGCTATGTCCTGAACAATATCCTTTGAAGGTGAATGGTCCTTGCCAGAAGGTGTAAGCCTGATCCAAGGCTATTGTGAAAACTGTAC   270
 S  Y  P  E  Q  Y  P  L  K  V  N  G  P  L  P  E  G  V  S  V  I  Q  G  Y  C  E  N  C  T
CATGTATCCTGAAGAAAATAGTGTATCGGCCATTCTCTGTCATCATCCACAAGATTATCGTATTGCAAGCCAGGCAGAGATTAAGGCACA   360
 M  Y  P  E  E  N  S  V  S  A  F  S  S  S  S  T  Q  D  Y  R  I  A  S  E  A  E  I  K  A  H
CACATTTTACACAGCATTGTCAGCCAATGCATACTGCAGAACTGTCATTCCTGGTGGTCGATGGAGCTGTCCCCACTGTGGTGTTGCATC   450
  T  F  Y  T  A  L  S  A  N  A  Y  C  R  T  V  I  P  G  G  R  W  S  C  P  H  C  G  V  A  S
CAATTTGCAAATTACCAAGACTTCAGCACCTTAATCACTGATACTAATGTCTTGGTGGTGTTGGCCAAAAGGAGAAGACCATCTATGT   540
  N  L  Q  I  T  K  T  F  S  T  L  I  T  D  T  N  V  L  V  A  V  G  E  K  E  K  T  I  Y  V
AGTTTTTCGTGGTACASGCTCAATTCGCAACGCCATTGCTGTAAGTTCACCCCCTTACAAACATGACACTTTCTTCCTCATCCCACTCATT   630
  V  F  R  G  T  S  S  I  R  N  A  I  A
CTTTCTTACAGGACATTGTTTTTGTACCAGTGAATTATCCACCTGTTAATGGAGCCAAAGTACACAAAGGTATGTGATGAGTGGTGTCA   720
  D  I  V  F  V  P  V  N  Y  P  P  V  N  G  A  K  V  H  K
```

FIG.6A

```
TTTATATATAAGAATGCTCAATATGCTCATTTACTATCTAGGATTTCTTGATAGCTATAACGAAGTCCAGGATAAACTTGTTGCTGAAGT     810
                G  F  L  D  S  Y  N  E  V  Q  D  K  L  V  A  E  V

CAAGGCACAACTTGATCGTCATCCAGGATACAAGATCGTCGTCACTGGGTAAATACCTGAAAAGACATGGCACGTGACTAAATCTG        900
K  A  Q  L  D  R  H  P  G  Y  K  I  V  V  T  G

TGTCATTGGTAGACATTCCTTGGGAGTGCAACAGCTGTCTCAGTGCACTTTATCACCATGGCCATGCCAATATCGAAATCTA              990
   H  S  L  G  G  A  T  A  V  L  S  A  L  D  L  Y  H  H  G  H  A  N  I  E  I  Y

TACTCAAGGTCAGCCACGTATAGGTACTCCAGGCATTTGCAAACTATGTGATTGGCACCAAGATTCCATACCAACGTCTTGTCCATGAGCG    1080
T  Q  G  Q  P  R  I  G  T  P  A  F  A  N  Y  V  I  G  T  K  I  P  Y  Q  R  L  V  H  E  R

TGACAGTAAGTGTACCTTGCACGACACATGTCGTTTCCCGACTACTAAAGTATTGTATAGTTGTTCCTCACCTTCCACCTGGTGCATT       1170
D                                              V  P  H  L  P  P  G  A  F

TGGTTTCTTGCATGCTGGTGAAGAGTTTTGGATCATGAAAGATAGCTCGTTGCGTAAGTAGTGTCATTGAAAAGGTTGAAGCTATAATAC     1260
G  F  L  H  A  G  E  E  F  W  I  M  K  D  S  S  L

TGACTATATTGGGTAGGCCTAGCCCTATGCCAAATGCCATTGAAACTGACAACTGCAGCAACTCCATGTTCCCTTCACTAGTGTCATTGACCAT 1350
                R  V  C  P  N  G  I  E  T  D  N  C  S  N  S  I  V  P  F  T  S  V  I  D  H

TTAAGGTGAATAGTAGCTTTATTCATGTCATTCATCCATGTAAACTAACACTTGTCGTATCTAGCTATCTTGACATGAACACTGGTCTCT     1440
L  S                                            Y  L  D  M  N  T  G  L

GTTTATAAATCTTTAGTATCATCCACTCCTCCCTCTTTAATGCAATACTTTTTAAGATAAATCACAAGTATACTTTGTACAAACCAATCAA    1530
C  L

ATGGCTTTTATTAGATGTGAAAAAGGATGACTAAATGACTAAATTAAAGAGTTTAGTCGAAAAGACCGAAGCCCATATCTCATCAGATTCCT   1620

CGGCCTCTTCCTTGACTTCTTCCTTCTTGTCATCAGCAGCAGCAGCGGGAGCAGCAACAACGAAAGCATCAGGGTTCTCCAAGA           1710
```

ATCC 1714

FIG.6B

```
          10         20         30         40         50         60
    *     *    *     *    *     *    *     *    *     *    *     *
AAAGGCATTC TCATTTTGTA GTCTTATTGC TAGCAGTATT CATCTGCATG TGCTCTGTAT 70         80         90        100        110        120
    *     *    *     *    *     *    *     *    *     *    *     *
CGGGTGTGCC ACTGCAAATT GATCCACGCG ATGACAAGAG CTATGTTCCT GAACAATATC 130        140        150        160        170        180
    *     *    *     *    *     *    *     *    *     *    *     *
CTTTGAAGGT GAATGGTCCT TTGCCAGAAG GTGTAAGCGT GATCCAAGGC TATTGTGAAA 190        200        210        220        230        240
    *     *    *     *    *     *    *     *    *     *    *     *
ACTGTACCAT GTATCCTGAA AAAAATAGTG TATCGGCATT CTCGTCATCA TCCACACAAG 250        260        270        280        290        300
    *     *    *     *    *     *    *     *    *     *    *     *
ATTATCGTAT TGCAAGCGAG GCAGAGATTA AGGCACACAC ATTTTACACA GCATTGTCAG 310        320        330        340        350        360
    *     *    *     *    *     *    *     *    *     *    *     *
CCAATGCATA CTGCAGAACT GTCATTCCTG GTGGTCGATG GAGCTGTCCC CACTGTGGTG 370        380        390        400        410        420
    *     *    *     *    *     *    *     *    *     *    *     *
TTGCATCCAA TTTGCAAATT ACCAAGACTT TCAGCACCTT AATCACTGAT ACTAATGTCT 430        440        450        460        470        480
    *     *    *     *    *     *    *     *    *     *    *     *
TGGTGGCTGT TGGCGAAAAG GAGAAGACCA TCTATGTAGT TTTTCGTGGT ACAAGCTCAA 490        500        510        520        530        540
    *     *    *     *    *     *    *     *    *     *    *     *
TTCGCAACGC CATTGCTGAC ATTGTTTTTG TACCAGTGAA TTATCCACCT GTTAATGGAG 550        560        570        580        590        600
    *     *    *     *    *     *    *     *    *     *    *     *
CCAAAGTACA CAAAGGATTT CTTGATAGCT ATAACGAAGT CCAGGATAAA CTTGTTGCTG
```

FIG.7A

```
        610        620        630        640        650        660
   *      *    *      *    *      *    *      *    *      *    *      *
AAGTCAAGGC ACAACTTGAT CGTCATCCAG GATACAAGAT CGTCGTCACT GGACATTCCT 670        680        690        700        710        720
   *      *    *      *    *      *    *      *    *      *    *      *
TGGGAGGTGC AACAGCTGTT CTCAGTGCAC TTGACCTTTA TCACCATGGC CATGCCAATA 730        740        750        760        770        780
   *      *    *      *    *      *    *      *    *      *    *      *
TCGAAATCTA TACTCAAGGT CAGCCACGTA TAGGTACTCC AGCATTTGCA AACTATGTGA 790        800        810        820        830        840
   *      *    *      *    *      *    *      *    *      *    *      *
TAGGCACCAA GATTCCATAC CAACGTCTTG TCCATGAGCG TGACATTGTT CCTCACCTTC 850        860        870        880        890        900
   *      *    *      *    *      *    *      *    *      *    *      *
CACCTGGTGC ATTTGGTTTC TTGCATGCTG GTGAAGAGTT TTGGATCATG AAAGATAGCT 910        920        930        940        950        960
   *      *    *      *    *      *    *      *    *      *    *      *
CGTTGCGCGT ATGTCCAAAT GGCATTGAAA CTGACAACTG CAGCAACTCC ATTGTTCCCT 970        980        990       1000       1010       1020
   *      *    *      *    *      *    *      *    *      *    *      *
TCACTAGTGT CATTGACCAT TTAAGCTATC TTGACATGAA CACTGGTCTC TGTTTATAAT 1030       1040       1050       1060       1070       1080
   *      *    *      *    *      *    *      *    *      *    *      *
CTTTAGTATC ATCCACTCCT CCTCTTTAAT GCAATACTTT TTAAGATAAA TCACAAGTAT 1090       1100       1110
   *      *    *      *    *      *    *
ACTTTGTACA AAACCAAAAA AAAAAAAAAA AAAAA
```

FIG.7B

```
          10         20         30         40         50         60
     *    *     *    *     *    *     *    *     *    *     *    *
RHSHFVVLLL AVFICMCSVS GVPLQIDPRD DKSYVPEQYP LKVNGPLPEG VSVIQGYCEN 70         80         90        100        110        120
     *    *     *    *     *    *     *    *     *    *     *    *
CTMYPEKNSV SAFSSSSTQD YRIASEAEIK AHTFYTALSA NAYCRTVIPG GRWSCPHCGV 130        140        150        160        170        180
     *    *     *    *     *    *     *    *     *    *     *    *
ASNLQITKTF STLITDTNVL VAVGEKEKTI YVVFRGTSSI RNAIADIVFV PVNYPPVNGA 190        200        210        220        230        240
     *    *     *    *     *    *     *    *     *    *     *    *
KVHKGFLDSY NEVQDKLVAE VKAQLDRHPG YKIVVTGHSL GGATAVLSAL DLYHHGHANI 250        260        270        280        290        300
     *    *     *    *     *    *     *    *     *    *     *    *
EIYTQGQPRI GTPAFANYVI GTKIPYQRLV HERDIVPHLP PGAFGFLHAG EEFWIMKDSS 310        320        330
     *    *     *    *     *    *     *
LRVCPNGIET DNCSNSIVPF TSVIDHLSYL DMNTGLCL
```

FIG.7C

```
  1  M - - - - - - - - H S Y I L V L L A V F I C T S S V L G V P M Q I    A.blakesleeana.lip
  1  M - - - - - - - - R F Y S V V S L L A V F I C T Y G V S G V P V Q I  A.griseola v iguchii.lip
  1  M - - - - - - - - H S H F V V L L A V F I C T C S V L G V P L Q I    A.corymbifera.lip
  1  M - - - - - - - - H S H F V V L L A V F I C M C S V S G V P L Q I    A.sporophora-variabilis.lip
  1  M V L K Q R A N Y L G F L I - V F F T A F L V E A V P I K R          R.miehei.lip
  1  M R - - - - - - - - - - - - S S L V L F F V S A W T A L A S P I R R H.lanuginosa.lip 27  D Q R D K K S Y V P E Q Y P - - - - - - - - - - - - - - - - - -      A.blakesleeana.lip
 27  G P R D - K S Y V P E Q Y P - - - - - - - - - - - - - - - - - -      A.griseola v iguchii.lip
 27  D P R D D K S Y V P E Q Y P - - - - - - - - - - - - - - - - - -      A.corymbifera.lip
 27  D P R D D K S Y V P E Q Y P - - - - - - - - - - - - - - - - - -      A.sporophora-variabilis.lip
 30  Q S N S T V D S L P P L I P S R T S A P S S S P S T T D P E          R.miehei.lip
 23  E V S Q D - - - - - - - - - - - - - - - - - - - - - - - - - -       H.lanuginosa.lip 41  - - - L K M N G P L P E G V S K I Q G Y C E N C T M Y P E E          A.blakesleeana.lip
 40  - - - L K M N G P L P E G V S V I Q G Y C E N C T M Y P E E          A.griseola v iguchii.lip
 41  - - - L K V N G P L P E G V S V I Q G Y C E N C T M Y P E E          A.corymbifera.lip
 41  - - - L K V N G P L P E G V S V I Q G Y C E N C T M Y P E E          A.sporophora-variabilis.lip
 60  A P A M S R N G P L P S D V E T K Y G M A L N A T S Y P D -          R.miehei.lip
 28  - - - - - - - - - - L F N Q F N L F A Q Y S A - - A A Y C G K       H.lanuginosa.lip
```

```
242  YTQGQPRVGTPAFANYV--IGTKIPYQRLVN   A.blakesleeana.lip
241  YTQGQPRVGTPAFANYV--IGTKIPYQRLVN   A.griseola v iguchii.lip
243  YTQGQPRIGTPEFANYV--IGTKIPYQRLVN   A.corymbifera.lip
243  YTQGQPRVGDPAFANYV--IGTKIPYQRLVH   A.sporophora-variabilis.lip
266  YTQGQPRVGNRAFANYV--VSTGIPYRRTVN   R.miehei.lip
191  FSYGAPRVGNRAFAEFLTVQIGGTLYRITH    H.lanuginosa.lip 271  ERDIVPHLPPGAFGGLHAGEEFWIMKDN--    A.blakesleeana.lip
270  ERDIVPHLPPGAFGFLHAGEEFWIMKDS--    A.griseola v iguchii.lip
272  ERDIVPHLPPGAFGFLHAGEEFWIMKDN--    A.corymbifera.lip
272  ERDIVPHLPPGAFGFLHAGEEFWIMKDS--    A.sporophora-variabilis.lip
295  ERDIVPHLPPAAFGFLHAGEEYWITDNS--    R.miehei.lip
221  TNDIVPRLPPREFGYSHSSPEYWIKSGTLV    H.lanuginosa.lip 299  ----S--LRVCPNGIETDDCSNSIVPFTSV    A.blakesleeana.lip
298  ----S--LRVCPNGIETDDCSNSIVPFTSV    A.griseola v iguchii.lip
300  ----S--LRVCPNGIETDNCSNSIVPFTSV    A.corymbifera.lip
300  ----S--LRVCPNGIETDNCSNSIVPFTSV    A.sporophora-variabilis.lip
323  ----PETVQVCTSDLETSDCSNSIVPFTSV    R.miehei.lip
251  PVTRNDIVKI--EGIDATG-GNNQPNIPDI    H.lanuginosa.lip 323  IDHLSYLDMNTGLCL                   A.blakesleeana.lip
322  IDHLSYLDMNTGLCL                   A.griseola v iguchii.lip
324  IDHLSYLDMNTGLCL                   A.corymbifera.lip
324  IDHLSYLDMNTGLCL                   A.sporophora-variabilis.lip
349  LDHLSYFGINTGLCT                   R.miehei.lip
278  PAHLWYFGL-IGTCL                   H.lanuginosa.lip
```

NUCLEIC ACIDS ENCODING POLYEPTIDES HAVING ABSIDIA LIPASE ACTIVITY

CROSS-REFERENCE TO RELATED APPLICATIONS

This application claims the benefit of U.S. Patent Application Ser. No. 60/013,616, filed Jan. 24, 1996, which is herein incorporated by reference.

BACKGROUND OF THE INVENTION

1. Field of the Invention

The present invention relates to isolated nucleic acid sequences encoding polypeptides having *Absidia* lipase activity. The invention also relates to nucleic acid constructs, vectors, and host cells comprising the nucleic acid sequences as well as recombinant methods for producing the polypeptides.

2. Description of the Related Art

Detergents formulated with lipolytic enzymes are known to have improved properties for removing fatty stains. For example, LIPOLASE™ (Novo Nordisk A/S, Bagsvaerd, Denmark), a microbial lipase obtained from the fungus *Thermomyces lanuginosus* (also called *Humicola lanuginosa*), has been introduced into many commercial brands of detergent.

Other microbial lipases from *Pseudomonas cepacia* (U.S. Pat. No. 4,876,024), *Streptomycetes* (WO94/14940), and *Gongronella butleri* strain NRRL 3521 (U.S. Pat. No. 3,634,195, the strain was previously named *Absidia butleri*, see K. H. Domsch et al., *Compendium of Soil Fungi*, Academic Press 1980, p. 381) have also been suggested for use in detergents.

U.S. Pat. No. 3,634,195 describes the production of lipase from *Absidia cylindrospora* var. *rhizomorpha* NRRL 2815 and *Absidia blakesleeana* NRRL 1305. Koritala et al. (1987, *Journal of the American Oil Chemists Society* 64:509–513) disclose that soybean oil was partially hydrolyzed when incubated with *Absidia coerula* NRRL 5926 and *Absidia ramosa* NRRL 1309. Satyanarayana (1981, *Current Science* 50:680–682) discloses the secretion of lipase by a strain of *Absidia corymbifera*. Aisaka et al. (1979, *Agricultural Biological Chemistry* 43:2125–2129) described the formation of a lipoprotein lipase from *Absidia hyalospora* strain KY 303 (now classified as *Absidia blakesleeana*).

Many detergents are alkaline in solution (e.g., around pH 10) and contain a builder to bind $Ca^{++}$ ions. There is a need for new lipolytic enzymes with high activity at high pH in the absence of $Ca^{++}$. Lipases of the genus *Absidia* possess these characteristics, and therefore, are highly desirable for use in detergent compositions. Heretofore, however, there has been no means of producing these enzymes recombinantly.

It is an object of the present invention to provide for recombinant production of these valuable enzymes.

SUMMARY OF THE INVENTION

The present invention relates to isolated nucleic acid sequences encoding polypeptides having lipase activity selected from the group consisting of:

(a) a nucleic acid sequence which encodes a polypeptide endogenous to an *Absidia* strain with an amino acid sequence set forth in SEQ ID NO:2, SEQ ID NO:4, SEQ ID NO:6, SEQ ID NO:8, or SEQ ID NO:10;

(b) a nucleic acid sequence endogenous to an *Absidia* strain which is capable of hybridizing under medium stringency conditions with (i) the nucleic acid sequence set forth in SEQ ID NO:1, SEQ ID NO:3, SEQ ID NO:5, SEQ ID NO:7, or SEQ ID NO:9 or (ii) any of their complementary strands;

(c) a nucleic acid sequence which is capable of hybridizing under medium stringency conditions with (i) the nucleic acid sequence set forth in SEQ ID NO:1, SEQ ID NO:3, SEQ ID NO:5, SEQ ID NO:7, or SEQ ID NO:9 or (ii) any of their complementary strands;

(d) a nucleic acid sequence encoding a polypeptide having lipase activity with an amino acid sequence which has at least 65% identity with the amino acid sequence set forth in SEQ ID NO:2, SEQ ID NO:4, SEQ ID NO:6, SEQ ID NO:10;

(e) an allelic form of (a), (b), (c), or (d); and (f) a fragment of (a), (b), (c), (d), or (e).

The present invention also relates to nucleic acid constructs, vectors, and host cells comprising the nucleic acid sequences as well as recombinant methods for producing the polypeptides.

BRIEF DESCRIPTION OF THE FIGURES

FIG. 3 shows the DNA sequence and deduced amino acid sequence of *Absidia griseola* var. *iguchii* lipase (SEQ ID NOS. 1 and 2, respectively). Introns are marked by a solid line. Regions corresponding to previously determined peptide sequences are underlined (---).

FIG. 4 shows the DNA sequence and deduced amino acid sequence of *Absidia blakesleeana* lipase (SEQ ID NOS. 3 and 4, respectively). Introns are marked by a solid line. Regions corresponding to previously determined peptide sequences are underlined (---).

FIG. 5 shows the DNA sequence and deduced amino acid sequence of *Absidia corymbifera* lipase (SEQ ID NOS. 5 and 6, respectively). Introns are marked by a solid line. Regions corresponding to previously determined peptide sequences are underlined (---).

FIG. 6 shows the DNA sequence and deduced amino acid sequence of *Absidia sporophora-variabilis* lipase (SEQ ID NOS. 7 and 8, respectively). Introns are marked by a solid line.

FIGS. 7A and 7B show the DNA sequence and deduced amino acid sequence of *Absidia reflexa* lipase (SEQ ID NOS. 9 and 10, respectively).

FIG. 8 shows a comparison of the amino acid sequence homology among *Absidia* lipases compared to *Rhizomucor miehei* lipase (SEQ ID NO:15) and *Humicola lanuginosa* (SEQ ID NO:16). Identical residues are boxed.

DETAILED DESCRIPTION OF THE INVENTION

Nucleic Acid Sequences

Figure 1:
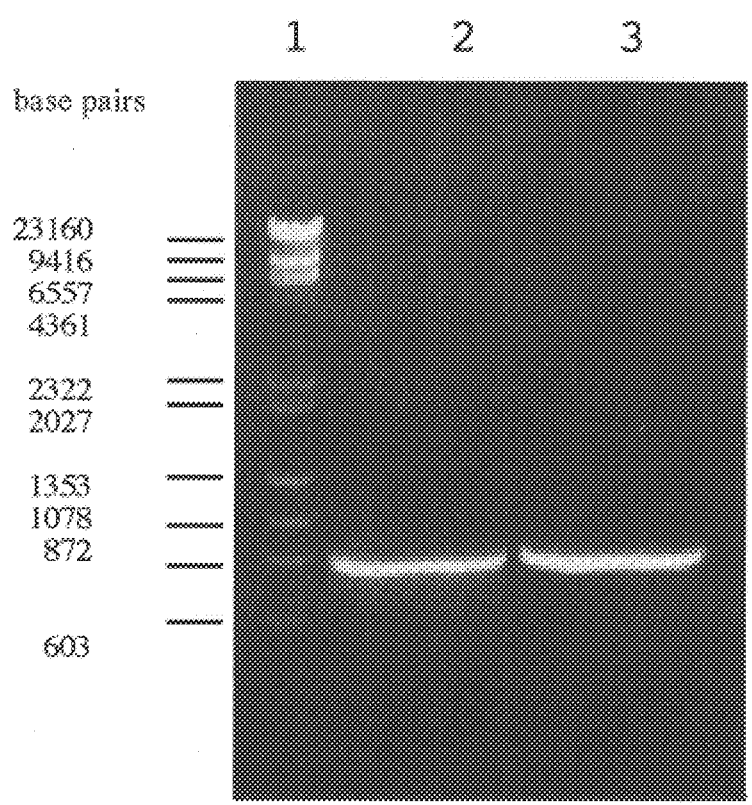
FIG. 1 shows an agarose gel purification of lipase-specific PCR products from *Absidia griseola* and *Absidia griseola* var. *iguchii* genomic DNA. Lane 1: HindIII-digested lambda DNA and HaeIII-digested φX17RF-DNA size standards; lane 2: *Absidia griseola* PCR product; and lane 3: *Absidia griseola* var. *Iguchii* PCR product. Both PCR products appear to be approximately 870 bp in size.

In a first embodiment, the present invention relates to isolated nucleic acid sequences which encode polypeptides having lipase activity with an amino acid sequences set forth in SEQ ID NO:2, SEQ ID NO:4, SEQ ID NO:6, SEQ ID NO:8, or SEQ ID NO:10. In a specific embodiment, the nucleic acid sequences are set forth in SEQ ID NO:1, SEQ ID NO:3, SEQ ID NO:5, SEQ ID NO:7, and SEQ ID NO:9. The nucleic acid sequences of the present invention also encompass nucleic acid sequences which encode a polypeptide having the amino acid sequence set forth in SEQ ID NO:2, SEQ ID NO:4, SEQ ID NO:6, SEQ ID NO:8, or SEQ ID NO:10, but differ from SEQ ID NO:1, SEQ ID NO:3, SEQ ID NO:5, SEQ ID NO:7, or SEQ ID NO: 9, respectively, by virtue of the degeneracy of the genetic code. The present invention also relates to subsequences of SEQ ID NO:1, SEQ ID NO:3, SEQ ID NO:5, SEQ ID NO:7, or SEQ ID NO:9, which encode a fragment of SEQ ID NO:2, SEQ ID NO:4, SEQ ID NO:6, SEQ ID NO:8, or SEQ ID NO:10, respectively, and retain lipase activity. In a preferred embodiment, the nucleic acid sequences of the present invention are the nucleic acid sequences contained in plasmids pZL-NL1, pZL-NL61, pZL-NL95, and pZL-NL124, which are contained in *Escherichia coli* NRRL B-21520, NRRL B-21521, NRRL B-21522, and NRRL B-21523, respectively.

The term "isolated nucleic acid sequence" as used herein refers to a nucleic acid sequence which is essentially free of other nucleic acid sequences, e.g., at least about 20% pure, preferably at least about 40% pure, more preferably at least about 60% pure, even more preferably at least about 80% pure, and most preferably at least about 90% pure as determined by agarose electrophoresis. For example, an isolated nucleic acid sequence can be obtained by standard cloning procedures used in genetic engineering to relocate the nucleic acid sequence from its natural location to a different site where it will be reproduced. The cloning procedures may involve excision and isolation of a desired nucleic acid fragment comprising the nucleic acid sequence encoding the polypeptide, insertion of the fragment into a vector molecule, and incorporation of the recombinant vector into a host cell where multiple copies or clones of the nucleic acid sequence will be replicated. The nucleic acid sequence may be of genomic, cDNA, RNA, semisynthetic, synthetic origin, or any combinations thereof.

The term "lipase" is defined herein as a lipolytic enzyme classified under the Enzyme Classification number E.C. 3.1.1.-(Carboxylic Ester Hydrolases) in accordance with the Recommendations (1992) of the International Union of Biochemistry and Molecular Biology (IUBMB). Lipolytic enzymes thus exhibit hydrolytic activity towards at least one of the types of ester bonds mentioned in the context of E.C. 3.1.1, for example, ester bonds present in mono-, di- and triglycerides, phospholipids (all classes), thioesters, cholesterol esters, wax-esters, cutin, suberin, synthetic esters, etc. As an example, the lipolytic enzymes of the present invention may have activity towards triglycerides lipase activity, E.C. 3.1.1.3), e.g., 1,3-positionally specific lipase activity.

In a second embodiment, the present invention relates to isolated nucleic acid sequences encoding polypeptides with lipase activity which are capable of hybridizing under high, medium, or low stringency conditions with an oligonucleotide probe which hybridizes under the same conditions with the nucleic acid sequence set forth in SEQ ID NO:1, SEQ ID NO:3, SEQ ID NO:5, SEQ ID NO:7, or SEQ ID NO:9, its complementary strand or a subsequence thereof (J. Sambrook, E. F. Fritsch, and T. Maniatis, 1989, *Molecular Cloning, A Laboratory Manual,* 2d edition, Cold Spring Harbor, New York). Hybridization indicates that the analogous nucleic acid sequence hybridizes to the oligonucleotide probe corresponding to the polypeptide encoding part of the nucleic acid sequence shown in SEQ ID NO:1, SEQ ID NO:3, SEQ ID NO:5, SEQ ID NO:7, or SEQ ID NO:9, under low to high stringency conditions (for example, prehybridization and hybridization at 42° C. in 5X SSPE, 0.3% SDS, 200 μg/ml sheared and denatured salmon sperm DNA, and either 50, 35 or 25% formamide for high, medium and low stringencies, respectively), following standard Southern blotting procedures. In a preferred embodiment, the nucleic acid sequences are capable of hybridizing under medium stringency conditions and most preferably under high stringency conditions. In another preferred embodiment, the nucleic acid sequences are capable of hybridizing with the nucleic acid sequence set forth in SEQ ID NO:1, SEQ ID NO:3, SEQ ID NO:5, SEQ ID NO:7, or SEQ ID NO:9, or its complementary strand.

SEQ ID NO:1, SEQ ID NO:3, SEQ ID NO:5, SEQ ID NO:7, or SEQ ID NO:9, as well as SEQ ID NO:2, SEQ ID NO:4, SEQ ID NO:6, SEQ ID NO:8, or SEQ ID NO:10, or subsequences thereof may be used to design an oligonucleotide probe to isolate homologous genes encoding lipases from other strains of different genera or species according to methods well known in the art. Thus a genomic or cDNA library prepared from such other organisms may be screened for DNA which hybridizes with such probes following standard Southern blotting procedures, in order to identify and isolate the corresponding gene therein. Such probes can be considerably shorter than the entire sequence, but should be at least 15, preferably at least 25, and more preferably at least 40 nucleotides in length. Longer probes, preferably no more than 1200 nucleotides in length, can also be used. Both DNA and RNA probes can be used. The probes are typically labeled for detecting the corresponding gene (for example, with $^{32}$P, $^{3}$H, biotin, or avidin). A PCR reaction using the degenerate probes mentioned herein and genomic DNA or first-strand cDNA from an *Absidia* strain can also yield an *Absidia* lipase-specific product which can then be used as a probe to clone the corresponding genomic or cDNA.

Genomic or other DNA from such other organisms may be separated by agarose or polyacrylamide gel electrophoresis, or other separation techniques. DNA from the libraries or the separated DNA may be transferred to and immobilized on nitrocellulose or other suitable carrier material. In order to identify clones or DNA which are homologous with SEQ ID NO:1, SEQ ID NO:3, SEQ ID NO:5, SEQ ID NO:7, or SEQ ID NO:9, the carrier material is used in a Souther blot in which the carrier material is finally washed three times for 30 minutes each using 2X SSC, 0.2% SDS at preferably not higher than 40° C., more preferably not higher than 45° C., more preferably not higher than 50° C., more preferably not higher than 55° C., even more preferably not higher than 60° C., especially not higher than 65° C. Molecules to which the oligonucleotide probe hybridizes under these conditions are detected using X-ray film.

The present invention also relates to isolated nucleic acid sequences which have a degree of identity to the nucleic acid sequence set forth in SEQ ID NO:1, SEQ ID NO:3, SEQ ID NO:5, SEQ ID NO:7, or SEQ ID NO:9 of at least about 65%, preferably about 70%, preferably about 75%, preferably about 80%, more preferably about 85%, even more preferably about 90%, most preferably about 95%, and even most preferably about 97%, which encode an active polypeptide. The degree of identity between two nucleic acid sequences may be determined by means of computer programs known in the art such as GAP provided in the GCG program package (Needleman and Wunsch, 1970, *Journal of Molecular Biology* 48:443–453). For purposes of determining the degree of identity between two nucleic acid sequences for the present invention, the Clustal method (DNASTAR, Inc., Madison, Wis.) is used with an identity table, a gap penalty of 10, and a gap length of 10.

In a third embodiment, the present invention relates to isolated nucleic acid sequences encoding polypeptides with lipase activity which have an amino acid sequence with a degree of identity to the amino acid sequence set forth in SEQ ID NO:2, SEQ ID NO:4, SEQ ID NO:6, SEQ ID NO:8, or SEQ ID NO:10 of at least about 65%, preferably about 70%, preferably about 75%, preferably about 80%, more preferably about 85%, even more preferably about 90%, most preferably about 95%, and even most preferably about 97%, which qualitatively retain the activity of the polypeptides (hereinafter "homologous polypeptides"). In a preferred embodiment, the homologous polypeptides have an amino acid sequence which differs by five amino acids, preferably by four amino acids, more preferably by three amino acids, even more preferably by two amino acids, and most preferably by one amino acid from the amino acid sequence set forth in SEQ ID NO:2, SEQ ID:NO:4, SEQ ID NO:6, SEQ ID NO:8, or SEQ ID NO:10. The degree of identity between two or more amino acid sequences may be determined by means of computer programs known in the art such as GAP provided in the GCG program package (Needleman and Wunsch, 1970, *Journal of Molecular Biology* 48:443–453). For purposes of determining the degree of identity between two amino acid sequences for the present invention, the Clustal method (DNASTAR, Inc., Madison, Wis.) is used with an identity table, a gap penalty of 10, and a gap length of 10.

The amino acid sequences of the homologous polypeptides encoded by the nucleic acid sequences of the present invention may differ from the amino acid sequence set forth in SEQ ID:NO:2, SEQ ID NO:4, SEQ ID NO:6, SEQ ID NO:8, or SEQ ID NO:10 by an insertion or deletion of one or more amino acid residues and/or the substitution of one or more amino acid residues by different amino acid residues. Preferably, amino acid changes are of a minor nature, that is conservative amino acid substitutions which do not significantly affect the folding and/or activity of the protein; small deletions, typically of one to about 30 amino acids; small amino- or carboxyl-terminal extensions, such as an amino-terminal methionine residue; a small linker peptide of up to about 20–25 residues; or a small extension that facilitates purification by changing net charge or another function, such as a poly-histidine tract, an antigenic epitope or a binding domain.

Examples of conservative substitutions are within the group of basic amino acids (such as arginine, lysine and histidine), acidic amino acids (such as glutamic acid and aspartic acid), polar amino acids (such as glutamine and asparagine), hydrophobic amino acids (such as leucine, isoleucine and valine), aromatic amino acids (such as phenylalanine, tryptophan and tyrosine), and small amino acids (such as glycine, alanine, serine, threonine and methionine). Amino acid substitutions which do not generally alter the specific activity are known in the art and are described, e.g., by H. Neurath and R. L. Hill, 1979, *In, The Proteins,* Academic Press, New York. The most commonly occurring exchanges are: Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, Asp/Gly as well as these in reverse.

The isolated nucleic acid sequences of the present invention which are capable of hybridizing with an oligonucleotide probe which hybridizes with the nucleic acid sequence set forth in SEQ ID NO:1, SEQ ID NO:3, SEQ ID NO:5, SEQ ID NO:7, or SEQ ID NO:9, its complementary strand or a subsequence thereof, may be obtained from microorganisms of any genus, for example, from a bacterial or fungal source, but preferably from a fungal cell, and more preferably from a filamentous fungal cell or a yeast cell. For purposes of the present invention, the term "obtained from" (or endogenous to) as used herein in connection with a given source shall means that the polypeptide is produced by the source or by a cell in which a gene from the source has been inserted. Preferred sources for homologous genes are strains of the genus *Absidia* and species thereof available in public depositories. Furthermore, homologous genes may be identified and obtained from other sources including microorganisms isolated from nature (e.g., soil, composts, water, etc.) using the above-mentioned probes. Techniques for isolating microorganisms from natural habitats are well known in the art. The nucleic acid sequence may then be derived by similarly screening a cDNA library of another microorganism. Particularly preferred strains are filamentous fungus strains, such as an *Acremonium, Aspergillus, Aureobasidum, Cryptococcus, Filibasidium, Fusarium, Humicola, Magnaporthe, Mucor, Myceliophthora, Neocalimastix, Neurospora, Paecilomyces, Penicillin, Piromyces, Schizophyllum, Talaromyces, Thermoascus, Thielavia, Tolypocladium,* or *Trichoderma* strain or yeast strains, such as a *Candida Kluyveromyces, Pichia, Saccharomyces, Schizosaccharomyces,* or *Yarrowia* strain.

In a preferred embodiment, a nucleic acid sequence of the present invention is obtained from a strain of the genus *Absidia,* as described in M. A. A. Schipper, Persoonia, Vol. 14, Part 2, pp. 133–148 (1990), such as a strain of *Absidia griseola, Absidia sporophora-variabilis, Absidia griseola* var. *iguchii, Absidia corymbifera,* or *Absidia blakesleeana.* In an even more preferred embodiment, the nucleic acid sequence is obtained from *Absidia blakesleeana* NN100826 (NRRL 1304), e.g., the nucleic acid sequence set forth in SEQ ID NO:3; *Absidia corymbifera* NN100062 (IFO 8084), e.g., the nucleic acid sequence set forth in SEQ ID NO:5; *Absidia griseola* NN000987 (ATCC 20430); *Absidia griseola* var. *iguchii* NN000591 (ATCC 20431), e.g., the nucleic acid sequence set forth in SEQ ID NO:1, *Absidia sporophora-variabilis* NN102427 (ATCC 36019), e.g., the nucleic acid sequence set forth in SEQ ID NO:7; and *Absidia reflexa* NN102427 (ATCC 44896), e.g., the nucleic acid sequence set forth in SEQ ID NO:9.

Within the genus *Absidia,* the following subgenera, groups, species and strains are preferred. Variants and mutants thereof capable of producing lipolytic enzyme are also encompassed. It is noted that a number of previously recognized species names were reclassified by Schipper, *Op. cit.,* and for convenience the previously used names of some strains are also listed below where multiple numbers in the same box indicate multiple deposits of the same strain.

| Subgenus, group | Species name | Previous species name | Inventors strain No. | Deposit number(s) |
|---|---|---|---|---|
| Subgenus Mycocladus | A. blakesleeana | A. blakesleeana | NN100826 | NRRL 1304, ATCC 10148a, CBS 100.28, CMI 111736 |
| | | A. blakesleeana | NN102406 | CBS 100.36 |
| | | A. blakesleeana | NN102407 | CBS 102.36, NRRL 2696 |
| | | A. blakesleeana | NN102408 | CBA 420.70 |
| | | A. blakesleeana | NN102413 | NRRL 1305 |
| | | A. griseola | NN000987 | ATCC 20430 |
| | | A. griseola | NN102403 | CBS 519.71, ATCC 22618, IFO 9472 |
| | | A. griseola var. iguchii | NN000591 | ATCC 20431 |
| | | A. hyalospora | NN102432 | CBS 173.67, NRRL 2916 |
| | A. blakesleeana var. atrospora | A. atrospora | NN102423 | CBS 518.71, ATCC 22617, IFO 9471 |
| | A. corymbifera | A. corymbifera | NN100060 | CBS 100.31, IFO 4009, NRRL 2982 |
| | | A. corymbifera | NN100062 | IFO 8084 |
| | | A. corymbifera | NN102404 | CBS 102.48 |
| | | A. corymbifera | NN102405 | CBS 582.65, ATCC 22574, NRRL 1309 |
| | | A. hesseltinii | NN102426 | CBS 958.68, ATCC 24263 |
| Subenus Absidia, Group B | A. cylindrospora var. rhizomorpha | — | NN102422 | CBS 154.63, NRRL 2815 |
| | A. pseudocylindrospora | — | NN102434 | ATCC 24169, CBS 100.62, NRRL 2770 |
| — | A. reflexa | — | NN102424 | ATCC 44896, IFO 5874 |
| — | A. sporophoravariabilis | — | NN102427 | ATCC 36019 |

The above-mentioned strains are readily accessible to the public in a number of culture collections, such as the American Type Culture Collection (ATCC), Deutsche Sammlung von Mikroorganismen und Zellkulturen GmbH (DSM), Centraalbureau Voor Schimmelcultures (CBS), and Agricultural Research Service Patent Culture Collection, Northern Regional Research Center (NRRL).

Once a nucleic acid sequence has been detected with the probe(s) described above, the sequence may be isolated or cloned by utilizing techniques which are well known to those of ordinary skill in the art (see, e.g., Sambrook et al., supra). The known techniques used to isolate or clone a nucleic acid sequence include isolation from genomic DNA, preparation from cDNA, or a combination thereof. The cloning of the nucleic sequences of the present invention from such genomic DNA can be effected, e.g., by using the well known polymerase chain reaction (PCR). See, for example, Innis et al., 1990, *A Guide to Methods and Application,* Academic Press, New York. The nucleic acid sequence may be cloned from a strain of *Absidia* producing the polypeptide, or another or related organism and thus, for example, may be an allelic or species variant of the polypeptide encoding region of the nucleic acid sequence.

Modification of the nucleic acid sequence encoding the polypeptide may be necessary for the synthesis of polypeptides substantially similar to the polypeptide. The term "substantially similar" to the polypeptide refers to non-naturally occurring forms of the polypeptide. These polypeptides may differ in some engineered way from the polypeptide isolated from its native source. For example, it may be of interest to synthesize variants of the polypeptide where the variants differ in specific activity, thermostability, oxidative stability, pH optimum, or the like using, for example, site-directed mutagenesis. The analogous sequence may be constructed on the basis of the nucleic acid sequence presented as the polypeptide encoding region of SEQ ID NO:1, SEQ ID NO:3, SEQ ID NO:5, SEQ ID NO:7, or SEQ ID NO:9, a sub-sequence thereof, and/or by introduction of nucleotide substitutions which do not give rise to another amino acid sequence of the polypeptide encoded by the nucleic acid sequence, but which corresponds to the codon usage of the host organism intended for production of the enzyme, or by introduction of nucleotide substitutions which may give rise to a different amino acid sequence. For a general description of nucleotide substitution, see, e.g., Ford et al., 1991, *Protein Expression and Purification* 2:95–107.

It will be apparent to those skilled in the art that such substitutions can be made outside the regions critical to the function of the molecule and still result in an active polypeptide. Amino acid residues essential to the activity of the polypeptide encoded by the isolated nucleic acid sequence of the invention, and therefore preferably not subject to substitution, may be identified according to procedures known in the art, such as site-directed mutagenesis or alanine-scanning mutagenesis (see, e.g., Cunningham and Wells, 1989, *Science* 244:1081–1085). In the latter technique mutations are introduced at every residue in the molecule, and the resultant mutant molecules are tested for lipase activity to identify amino acid residues that are critical to the activity of the molecule. Sites of substrate-enzyme interaction can also be determined by analysis of crystal structure as determined by such techniques as nuclear magnetic resonance analysis, crystallography or photoaffinity labelling (see, e.g., de Vos et al., 1992, *Science* 255:306–312; Smith et al., 1992, *Journal of Molecular Biology* 224:899–904; Wlodaver et al., 1992, *FEBS Letters* 309:59–64).

Polypeptides encoded by the nucleic acid sequences of the present invention also include fused polypeptides in which another polypeptide is fused at the N-terminus or the C-terminus of the polypeptide or fragmen thereof. A fused polypeptide is produced by fusing a nucleic acid sequence (or a portion thereof) encoding another polypeptide to a nucleic acid sequence (or a portion thereof) of the present invention. Techniques for producing fusion polypeptides are known in the art, and include, ligating the coding sequences encoding the polypeptides so that they are in frame and that expression of the fused polypeptide is under control of the same promoter(s) and terminator.

The polypeptides having lipolytic activity encoded by the nucleic acid sequences of this invention are characterized by having a high activity at alkaline pH (about pH 9–10), even in the absence of free $Ca^{++}$.

More specifically, these polypeptides have optimum lipolytic activity at about pH 9 or higher (have a higher activity at pH 9 than at pH 8) when tested in the absence of free $Ca^{++}$.

Certain preferred nucleic acid sequences encode polypeptides having lipase activity when tested at pH9 without free $Ca^{++}$. Such lipolytic enzymes can be obtained from strains of *Absidia* subgenus *Mycoladus,* e.g., the species and strains listed above.

Another group of preferred nucleic acid sequences encode polypeptides having a higher lipolytic activity at pH 10 than pH 9 in the absence of $Ca^{++}$. Such a nucleic acid sequence can be obtained from *Absidia reflexa* NN102427 (ATCC 44896).

A further group of preferred nucleic acid sequences encodes polypeptides retaining more than 90% residual activity after 30 minutes incubation at pH 10, 45° C. Such a sequence can be obtained from a strain of *Absidia sporophora-variabilis,* e.g., *Absidia sporophora-variabilis* NN102427 (ATCC 36019).

Nucleic Acid Constructs

The present invention also relates to nucleic acid constructs comprising a nucleic acid sequence of the present invention operably linked to one or more control sequences capable of directing the expression of the coding sequence in a suitable host cell under conditions compatible with the control sequences.

"Nucleic acid construct" is defined herein as a nucleic acid molecule, either single- or double-stranded, which is isolated from a naturally occurring gene or which has been modified to contain segments of nucleic acid which are combined and juxtaposed in a manner which would not otherwise exist in nature. The term nucleic acid construct may be synonymous with the term expression cassette when the nucleic acid construct contains all the control sequences required for expression of a coding sequence of the present invention. The term "coding sequence" as defined herein is a sequence which is transcribed into mRNA and translated into a polypeptide of the present invention when placed under the control of the appropriate control sequences. The boundaries of the coding sequence are generally determined by a translation start codon ATG at the 5'-terminus and a translation stop codon at the 3'-terminus. A coding sequence can include, but is not limited to, DNA, cDNA, and recombinant nucleic acid sequences.

An isolated nucleic acid sequence encoding a polypeptide of the present invention may be manipulated in a variety of ways to provide for expression of the polypeptide. Manipulation of the nucleic acid sequence encoding a polypeptide prior to its insertion into a vector may be desirable or necessary depending on the expression vector. The techniques for modifying nucleic acid sequences utilizing cloning methods are well known in the art.

The term "control sequences" is defined herein to include all components which are necessary or advantageous for expression of the coding sequence of the nucleic acid sequence. Each control sequence may be native or foreign to the nucleic acid sequence encoding the polypeptide. Such control sequences include, but are not limited to, a leader, a polyadenylation sequence, a propeptide sequence, a promoter, a signal sequence, and a transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleic acid sequence encoding a polypeptide.

The control sequence may be an appropriate promoter sequence, a nucleic acid sequence which is recognized by a host cell for expression of the nucleic acid sequence. The promoter sequence contains transcription control sequences which mediate the expression of the polypeptide. The promoter may be any nucleic acid sequence which shows transcriptional activity in the host cell of choice and may be obtained from genes encoding extracellular or intracellular polypeptides either homologous or heterologous to the host cell.

Examples of suitable promoters for directing the transcription of the nucleic acid constructs of the present invention, especially in a bacterial host cell, are the promoters obtained from the *E. coli* lac operon, the *Streptomyces coelicolor* agarase gene (dagA), the *Bacillus subtilis* levansucrase gene (sacB), the *Bacillus licheniformis* alpha-amylase gene (amyL), the *Bacillus stearothermophilus* maltogenic amylase gene (amyM), the *Bacillus amyloliquefaciens* alpha-amylase gene (amyQ), the *Bacillus licheniformis* penicillinase gene (penP), the *Bacillus subtilis* xylA and xylB genes, and the prokaryotic beta-lactamase gene (Villa-Kamaroff et al., 1978, *Proceedings of the National Academy of Sciences USA* 75:3727–3731), as well as the tac promoter (DeBoer et al., 1983, *Proceedings of the National Academy of Sciences USA* 80:21–25). Further promoters are described in "Useful proteins from recombinant bacteria" in *Scientific American,* 1980, 242:74–94; and in Sambrook et al., 1989, supra.

Examples of suitable promoters for directing the transcription of the nucleic acid constructs of the present invention in a filamentous fungal host cell are promoters obtained from the genes encoding *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium oxysporum* trypsin-like protease (as described in U.S. Pat. No. 4,288,627, which is incorporated herein by reference), and hybrids thereof. Particularly preferred promoters for use in filamentous fungal host cells are the TAKA amylase, NA2-tpi (a hybrid of the promoters from the genes encoding *Aspergillus niger* neutral a-amylase and *Aspergillus oryzae* triose phosphate isomerase), and glaA promoters.

In a yeast host, useful promoters are obtained from the *Saccharomyces cerevisiae* enolase (ENO-1) gene, the *Saccharomyces cerevisiae* galactokinase gene (GAL1), the *Saccharomyces cerevisiae* alcohol dehydrogenase/glyceraldehyde-3-phosphate dehydrogenase genes (ADH2/GAP), and the *Saccharomyces cerevisiae* 3-phosphoglycerate kinase gene. Other useful promoters for yeast host cells are described by Romanos et al., 1992, *Yeast* 8:423–488. In a mammalian host cell, useful promoters include viral promoters such as those from Simian Virus 40 (SV40), Rous sarcoma virus (RSV), adenovirus, and bovine papilloma virus (BPV).

The control sequence may also be a suitable transcription terminator sequence, a sequence recognized by a host cell to terminate transcription. The terminator sequence is operably linked to the 3' terminus of the nucleic acid sequence encoding the polypeptide. Any terminator which is functional in the host cell of choice may be used in the present invention.

Preferred terminators for filamentous fungal host cells are obtained from the genes encoding *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes encoding *Saccharomyces cerevisiae* enolase,

*Saccharomyces cerevisiae* cytochrome C (CYC1), or *Saccharomyces cerevisiae* glyceraldehyde-3-phosphate dehydrogenease. Other useful terminators for yeast host cell are described by Romanos et al., 1992, supra. Terminator sequences are well known in the art for mammalian host cells.

The control sequence may also be a suitable leader sequence, a nontranslated region of a mRNA which is important for translation by the host cell. The leader sequence is operably linked to the 5' terminus of the nucleic acid sequence encoding the polypeptide. Any leader sequence which is functional in the host cell of choice may be used in the present invention.

Preferred leaders for filamentous fungal host cells are obtained from the genes encoding *Aspergillus oryzae* TAKA amylase and *Aspergillus oryzae* triose phosphate isomerase.

Suitable leaders for yeast host cells are obtained from the *Saccharomyces cerevisiae* enolase (ENO-1) gene, the *Saccharomyces cerevisiae* 3-phosphoglycerate kinase gene, the *Saccharomyces cerevisiae* alpha-factor, and the *Saccharomyces cerevisiae* alcohol dehydrogenase/glyceraldehyde-3-phosphate dehydrogenase genes (ADH2/GAP).

The control sequence may also be a polyadenylation sequence, a sequence which is operably linked to the 3' terminus of the nucleic acid sequence and which, when transcribed, is recognized by the host cell as a signal to add polyadenosine residues to transcribed mRNA. Any polyadenylation sequence which is functional in the host cell of choice may be used in the present invention.

Preferred polyadenylation sequences for filamentous fungal host cells are obtained from the genes encoding *Aspergillus oryzae* TAKA amylase, *Aspergillus niger* glucoamylase, *Aspergillus nidulans* anthranilate synthase, and *Aspergillus niger* alpha-amylase.

Useful polyadenylation sequences for yeast host cells are described by Guo and Sherman, 1995, *Molecular Cellular Biology* 15:5983:5990. Polyadenylation sequences are well known in the art for mammalian host cells.

The control sequence may also be a signal peptide coding region, which codes for an amino acid sequence linked to the amino terminus of the polypeptide which can direct the expressed polypeptide into the cell's secretory pathway. The 5' end of the coding sequence of the nucleic acid sequence may inherently contain a signal peptide coding region naturally linked in translation reading frame with the segment of the coding region which encodes the secreted polypeptide. Alternatively, the 5' end of the coding sequence may contain a signal peptide coding region which is foreign to that portion of the coding sequence which encodes the secreted polypeptide. The foreign signal peptide coding region may be required where the coding sequence does not normally contain a signal peptide coding region. Alternatively, the foreign signal peptide coding region may simply replace the natural signal peptide coding region in order to obtain enhanced secretion of the lipase relative to the natural signal peptide coding region normally associated with the coding sequence. The signal peptide coding region may be obtained from a glucoamylase or an amylase gene from an *Aspergillus* species, a lipase or proteinase gene from a *Rhizomucor* species, the gene for the alpha-factor from *Saccharomyces cerevisiae*, an amylase or a protease gene from a *Bacillus* species, or the calf preprochymosin gene. However, any signal peptide coding region capable of directing the expressed lipase into the secretory pathway of a host cell of choice may be used in the present invention.

An effective signal peptide coding region for bacterial host cells is the signal peptide coding region obtained from the maltogenic amylase gene from *Bacillus* NCIB 11837, the *Bacillus stearothermophilus* alpha-amylase gene, the *Bacillus licheniformis* subtilisin gene, the *Bacillus licheniformis* beta-lactamase gene, the *Bacillus stearothermophilus* neutral proteases genes (nprT, nprS, nprM), and the *Bacillus subtilis* prsA gene. Further signal peptides are described by Simonen and Palva, 1993, *Microbiological Reviews* 57:109–137.

An effective signal peptide coding region for filamentous fungal host cells is the signal peptide coding region obtained from *Aspergillus oryzae* TAKA amylase gene, *Aspergillus niger* neutral amylase gene, the *Rhizomucor miehei* aspartic proteinase gene, the *Humicola lanuginosa* cellulase gene, or the *Rhizomucor miehei* lipase gene.

Useful signal peptides for yeast host cells are obtained from the genes for *Saccharomyces cerevisiae* alpha-factor and *Saccharomyces cerevisiae* invertase. Other useful signal peptide coding regions are described by Romanos et al., 1992, supra.

The control sequence may also be a propeptide coding region, which codes for an amino acid sequence positioned at the amino terminus of a polypeptide. The resultant polypeptide is known as a proenzyme or propolypeptide (or a zymogen in some cases). A propolypeptide is generally inactive and can be converted to mature active polypeptide by catalytic or autocatalytic cleavage of the propeptide from the propolypeptide. The propeptide coding region may be obtained from the *Bacillus subtilis* alkaline protease gene (aprE), the *Bacillus subtilis* neutral protease gene (nprT), the *Saccharomyces cerevisiae* alpha-factor gene, or the *Myceliophthora thermophilum* laccase gene (WO 95/33836).

The nucleic acid constructs of the present invention may also comprise one or more nucleic acid sequences which encode one or more factors that are advantageous in the expression of the polypeptide, e.g., an activator (e.g., a trans-acting factor), a chaperone, and a processing protease. Any factor that is functional in the host cell of choice may be used in the present invention. The nucleic acids encoding one or more of these factors are not necessarily in tandem with the nucleic acid sequence encoding the polypeptide.

An activator is a protein which activates transcription of a nucleic acid sequence encoding a polypeptide (Kudla et al., 1990, *EMBO Journal* 9:1355–1364; Jarai and Buxton, 1994, *Current Genetics* 26:2238–244; Verdier, 1990, *Yeast* 6:271–297). The nucleic acid sequence encoding an activator may be obtained from the genes encoding *Bacillus stearothermophilus* NprA (nprA), *Saccharomyces cerevisiae* heme activator protein 1 (hap1), *Saccharomyces cerevisiae* galactose metabolizing protein 4 (gal4), and *Aspergillus nidulans* ammonia regulation protein (areA). For further examples, see Verdier, 1990, supra and MacKenzie et al., 1993, *Journal of General Microbiology* 139:2295–2307.

A chaperone is a protein which assists another polypeptide in folding properly (Harl et al., 1994, TIBS 19:20–25; Bergeron et al., 1994, TIBS 19:124–128; Demolder et al., 1994, *Journal of Biotechnology* 32:179–189; Craig, 1993, *Science* 260:1902–1903; Gething and Sambrook, 1992, *Nature* 355:33–45; Puig and Gilbert, 1994, *Journal of Biological Chemistry* 269:7764–7771; Wang and Tsou, 1993, *The FASEB Journal* 7:1515–11157; Robinson et al., 1994, *Bio/Technology* 1:381–384). The nucleic acid sequence encoding a chaperone may be obtained from the genes encoding *Bacillus subtilis* GroE proteins, *Aspergillus oryzae* protein disulphide isomerase, *Saccharomyces cerevisiae* calnexin, *Saccharomyces cerevisiae* BiP/GRP78, and *Saccharomyces cerevisiae* Hsp70. For further examples, see Gething and Sambrook, 1992, supra, and Harl et al., 1994, supra.

A processing protease is a protease that cleaves a propeptide to generate a mature biochemically active polypeptide (Enderlin and Ogrydziak, 1994, Yeast 10:67–79; Fuller et al., 1989, Proceedings of the National Academy of Sciences USA 86:1434–1438; Julius et al., 1984, Cell 37:1075–1089; Julius et al., 1983, Cell 32:839–852). The nucleic acid sequence encoding a processing protease may be obtained from the genes Saccharomyces cerevisiae dipeptidylaminoeptidase, Saccharomyces cerevisiae Kex2, and Yarrowia lipolytica dibasic processing endoprotease (xpr6).

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems would include the lac, tac, and trp operator systems. In yeast, the ADH2 system or GAL1 system may be used. In filamentous fungi, the TAKA alpha-amylase promoter, Aspergillus niger glucoamylase promoter, and the Aspergillus oryzae glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleic acid sequence encoding the polypeptide would be placed in tandem with the regulatory sequence.

Expression Vectors

The present invention also relates to recombinant expression vectors comprising a nucleic acid sequence of the present invention, a promoter, and transcriptional and translational stop signals. The various nucleic acid and control sequences described above may be joined together to produce a recombinant expression vector which may include one or more convenient restriction sites to allow for insertion or substitution of the nucleic acid sequence encoding the polypeptide at such sites. Alternatively, the nucleic acid sequence of the present invention may be expressed by inserting the nucleic acid sequence or a nucleic acid construct comprising the sequence into an appropriate vector for expression. In creating the expression vector, the coding sequence is located in the vector so that the coding sequence is operably linked with the appropriate control sequences for expression, and possibly secretion.

The recombinant expression vector may be any vector (e.g., a plasmid or virus) which can be conveniently subjected to recombinant DNA procedures and can bring about the expression of the nucleic acid sequence. The choice of the vector will typically depend on the compatibility of the vector with the host cell into which the vector is to be introduced. The vectors may be linear or closed circular plasmids. The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. The vector system may be a single vector or plasmid or two or more vectors or plasmids which together contain the total DNA to be introduced into the genome of the host cell, or a transposon.

The vectors of the present invention may be integrated into the host cell genome when introduced into a host cell. For integration, the vector may rely on the nucleic acid sequence encoding the polypeptide or any other element of the vector for stable integration of the vector into the genome by homologous or nonhomologous recombination. Alternatively, the vector may contain additional nucleic acid sequences for directing integration by homologous recombination into the genome of the host cell. The additional nucleic acid sequences enable the vector to be integrated into the host cell genome at a precise location(s) in the chromosome(s). To increase the likelihood of integration at a precise location, the integrational elements should preferably contain a sufficient number of nucleic acids, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences. On the other hand, the vector may be integrated into the genome of the host cell by non-homologous recombination. These nucleic acid sequences may be any sequence that is homologous with a target sequence in the genome of the host cell, and, furthermore, may be non-encoding or encoding sequences.

For autonomous replication, the vector may further comprise an origin of replication enabling the vector to replicate autonomously in the host cell in question. Examples of bacterial origins of replication are the origins of replication of plasmids pBR322, pUC19, pACYC177, and pACYC184 permitting replication in E. coli, and pUB110, pE194, pTA1060, and pAMβ1 permitting replication in Bacillus. Examples of origin of replications for use in a yeast host cell are the 2 micron origin of replication, the combination of CEN6 and ARS4, and the combination of CEN3 and ARS1. The origin of replication may be one having a mutation which makes its functioning temperature-sensitive in the host cell (see, e.g., Ehrlich, 1978, Proceedings of the National Academy of Sciences USA 75:1433). In a specific embodiment, the expression vector may be pZL-NL1, pZL-NL61, pZL-NL95, or pZL-NL124.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like. Examples of bacterial selectable markers are the dal genes from Bacillus subtilis or Bacillus licheniformis, or markers which confer antibiotic resistance such as ampicillin, kanamycin, chloramphenicol or tetracycline resistance. A frequently used mammalian marker is the dihydrofolate reductase gene. Suitable markers for yeast host cells are ADE2, HIS3, LEU2, LYS2, MET3, TRP1, and URA3. A selectable marker for use in a filamentous fungal host cell may be selected from the group including, but not limited to, amdS (acetamidase), argB (ornithine carbamoyltransferase), bar (phosphinothricin acetyltransferase), hygB (hygromycin phosphotransferase), niaD (nitrate reductase), pyrG (orotidine-5'-phosphate decarboxylase), sC (sulfate adenyltransferase), trpC (anthranilate synthase), and glufosinate resistance markers, as well as equivalents from other speciies. Preferred for use in an Aspergillus cell are the amdS and pyrG markers of Aspergillus nidulans or Aspergillus oryzae and the bar marker of Streptomyces hygroscopicus. Furthermore, selection may be accomplished by co-transformation, e.g., as described in WO91/17243, where the selectable marker is on a separate vector.

More than one copy of a nucleic acid sequence encoding a polypeptide of the present invention may be inserted into the host cell to amplify expression of the nucleic acid sequence. Stable amplification of the nucleic acid sequence can be obtained by integrating at least one additional copy of the sequence into the host cell genome using methods well known in the art and selecting for transformants.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a nucleic acid sequence of the invention, which are advantageously used in the recombinant production of the polypeptides. The term "host cell" encompasses any progeny of a parent cell which is not identical to the parent cell due to mutations that occur during replication.

The cell is preferably transformed with a vector comprising a nucleic acid sequence of the invention followed by integration of the vector into the host chromosome. "Transformation" means introducing a vector comprising a nucleic acid sequence of the present invention into a host cell so that the vector is maintained as a chromosomal integrant or as a self-replicating extra-chromosomal vector. Integration is generally considered to be an advantage as the nucleic acid sequence is more likely to be stably maintained in the cell. Integration of the vector into the host chromosome occurs homolgous or non-homologous recombination as described above.

The choice of a host cell will to a large extent depend upon the gene encoding the polypeptide and its source. The host cell may be a unicellular microorganism, e.g., a prokaryote, or a non-unicellular microorganism, e.g., a eukaryote. Useful unicellular cells are bacterial cells such as gram positive bacteria including, but not limited to, a *Bacillus* cell, e.g., *Bacillus alkalophilus, Bacillus amyloliquefaciens, Bacillus brevis, Bacillus circulans, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* and *Bacillus thuringiensis;* or a *Streptomyces* cell, e.g., *Streptomyces lividans* or *Streptomyces murinus,* or gram negative bacteria such as *E. coli* and *Pseudomonas* sp. In a preferred embodiment, the bacterial host cell is a *Bacillus lentus, Bacillus licheniformis, Bacillus stearothermophilus* or *Bacillus subtilis* cell. The transformation of a bacterial host cell may, for instance, be effected by protoplast transformation (see, e.g., Chang and Cohen, 1979, Molecular General Genetics 168:111–115), by using competent cells (see, e.g., Young and Spizizin, 1061, *Journal of Bacteriology* 81:823–829, or Dubnau and Davidoff-Abelson, 1971, *Journal of Molecular Biology* 56:209–221), by electroporation (see, e.g., Shigekawa and Dower, 1988, *Bioltechniques* 6:742–751), or by conjugation (see, e.g., Koehler and Thorne, 1987, *Journal of Bacteriology* 169:5771–5278).

The host cell may be a eukaryote, such as a mammalian cell, an insect cell, a plant cell or a fungal cell. Useful mammalian cells include Chinese hamster ovary (CHO) cells, HeLa cells, baby hamster kidney (BHK) cells, COS cells, or any number of other immortalized cell lines available, e.g., from the American Type Culture Collection.

In a preferred embodiment, the host cell is a fungal cell. "Fungi" as used herein includes the phyla *Ascomycota, Basidomycota, Chytridiomycota,* and *Zygomycota* (as defined by Hawksworth et al., In, *Ainsworth and Bisby's Dictionary of the Fungi,* 8th edition, 1995, CAB International, University Press, Cambridge, UK) as well as the *Oomycota* (as cited in Hawksworth et al., 1995, supra, page 171) and all mitosporic fungi (Hawksworth et al., 1995, supra). Representative groups of *Ascomycota* include, e.g., *Neurospora, Eupenicillium (=Penicillium), Emericella (=Aspergillus), Eurotium (=Aspergillus),* and the true yeasts listed above. Examples of *Basidiomycota* include mushrooms, rusts, and smuts. Representative groups of *Chytridiomycota* include, e.g., *Allomyces, Blastocladiella, Coelomomyces,* and aquatic fungi. Representative groups of *Oomycota* include, e.g., *Saprolegniomycetous aquatic fungi* (water molds) such as *Achlya.* Examples of mitosporic fungi include *Aspergillus, Penicillium, Candida,* and *Alternaria.* Representative groups of *Zygomycota* include, e.g., *Rhizopus* and *Mucor.*

In a preferred embodiment, the fungal host cell is a yeast cell. "Yeast" as used herein includes ascosporogenous yeast (Endomycetales), basidiosporogenous yeast, and yeast belonging to the Fungi Imperfecti (Blastomycetes). The ascosporogenous yeasts are divided into the families Spermophthoraceae and Saccharomycetaseae. The latter is comprised of four subfamilies, Schizosacharomycoideae (e.g., genus *Schizosaccharomyces*), Nadsonioideae, Lipomycoideae, and Saccharomycoideae (e.g., genera *Pichia, Kluyveromyces* and *Saccharomyces*). The basidiosporogenous yeasts include the genera *Leucosporidim, Rhodosporidium, Sporidiobolus, Filobasidium,* and *Filobasidiella.* Yeast belonging to the Fungi Imperfecti are divided into two families, Sporobolomycetadeae (e.g., genera *Sorobolomyces* and *Bullera*) and Cryptococcaceae (e.g., genus *Candida*). Since the classification of yeast may change in the future, for the purposes of this invention, yeast shall be defined as described in *Biology and Activities of Yeast* (Skinner, F. A., Passmore, S. M., and Davenport, R. R., eds, Soc. App. Bacteriol. Symposium Series No. 9, 1980. The biology of yeast and manipulation of yeast genetics are well known in the art (see, e.g., *Biochemistry and Genetics of Yeast,* Bacil, M., Horecker, B. J., and Stopani, A. O. M., editors, 2nd edition, 1987; *The Yeasts,* Rose, A. H., and Harrison, J. S., editors, 2nd edition, 1987; and *The Molecular Biology of the Yeast Saccharomyces,* Strathern et al., editors, 1981).

In a more preferred embodiment, the yeast host cell is a cell of a species of *Candida, Kluyveromyces, Saccharomyces,, Schizosaccharomyces, Pichia,* or *Yarrowia.*

In a most preferred embodiment, the yeast host cell is a *Saccharomyces carlsbergensis, Saccharomyces cerevisiae, Saccharomyces diastaticus, Saccharomyces douglasii, Saccharomyces kluyveri, Saccharomyces norbensis* or *Saccharomyces oviformis* cell. In another most preferred embodiment, the yeast host cell is a *Kluyveromyces lactis* cell. In another most preferred embodiment, the yeast host cell is a *Yarrowia lipolytica* cell.

In a preferred embodiment, the fungal host cell is a filamentous fungal cell. "Filamentous fungi" include all filamentous forms of the subdivision Eumycota and Oomycota (as defined by Hawksworth et al., 1995, supra). The filamentous fungi are characterized by a vegetative mycelium composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative. In a more preferred embodiment, the filamentous fungal host cell is a cell of a species of, but not limited to, Acremonium, Aspergillus, Fusarium, Humicola, Mucor, Myceliophthora, Neurospora, Penicillium, Thielavia, Tolypocladiu, and Trichoderma.

In an even more preferred embodiment, the filamentous fungal host cell is an Aspergillus cell. In another even more preferred embodiment, the filamentous fungal host cell is an Acremonium cell. In another even more preferred embodiment, the filamentous fungal host cell is a Fusarium cell. In another even more preferred embodiment, the filamentous fungal host cell is a Humicola cell. In another even more preferred embodiment, the filamentous fungal host cell is a Mucor cell. In another even more preferred embodiment, the filamentous fungal host cell is a Myceliophthora cell. In another even more preferred embodiment, the filamentous fungal host cell is a Neurospora cell. In another even more preferred embodiment, the filamentous fungal host cell is a Penicillium cell. In another even more preferred embodiment, the filamentous fungal host cell is a Penicillium cell. In another even more preferred embodiment, the filamentous fungal host cell is a Thielavia cell. In another even more preferred embodiment, the filamentous fungal host cell is a Tolypocladium cell. In another even more preferred embodiment, the filamentous fungal host cell is a Trichoderma cell.

In a most preferred embodiment, the filamentous fungal host cell is an *Aspergillus awamori, Aspergillus foetidus, Aspergillus japonicus, Aspergilus nidulans, Aspergilus niger* or *Aspergillus oryzae* cell. In another most preferred embodiment, the filamentous fungal host cell is a *Fusarium cerealis, Fusarium crookwellense, Fusarium graminearum, Fusarium oxysporum, Fusarium sambucinum* or *Fusarium sulphureum* cell. In another most preferred embodiment, the filamentous fungal host cell is a *Humicola insolens* or *Humicola lanuginosa* cell. In another most preferred embodiment, the filamentous fungal host cell is a *Mucor miehei* cell. In another most preferred embodiment, the filamentous fungal host cell is a *Myceliophthora thermophilum* cell. In another most preferred embodiment, the filamentous fungal host cell is a *Neurospora crassa* cell. In another most preferred embodiment, the filamentous fungal host cell is a *Penicillium purpurogenum* cell. In another most preferred embodiment, the filamentous fungal host cell is a *Thielavia terrestris* cell. In another most preferred embodiment, the Trichoderma cell is a *Trichoderma harzianum, Trichoderma koningii, Trichoderma longibrachiatum, Trichoderma reesei* or *Trichoderma viride* cell.

Fungal cells may be transformed by a process involving protoplast formation, transformation of the protoplasts, and regeneration of the cell wall in a manner known per se. Suitable procedures for transformation of Aspergillus host cells are described in EP 238 023 and Yelton et al., 1984, *Proceedings of the National Academy of Sciences USA* 81:1470–1474. A suitable method of transforming Fusarium species is described by Malardier et al., 1989, *Gene* 78: 147–156 or in copending U.S. Ser. No. 08/269,449, incorporated herein by reference. Yeast may be transformed using the procedures described by Becker and Guarente, In Abelson, J. N. and Simon, M. I., editors, *Guide to Yeast Genetics and Molecular Biology,* Methods in Enzymology, Volume 194, pp 182–187, Academic Press, Inc., New York; Ito et al., 1983, *Journal of Bacteriology* 153: 163; and Hinnen et al., 1978, *Proceedings of the National Academy of Sciences USA* 75: 1920. Mammalian cells may be transformed by direct uptake using the calcium phosphate precipitation method of Graham and Van der Eb (1978, *Virology* 52: 546).

METHODS OF PRODUCTION

The present invention also relates to methods for producing a polypeptide of the present invention comprising (a) cultivating a host cell under conditions conducive to expression of the polypeptide; and (b) recovering the polypeptide.

In these methods, the cells are cultivated in a nutrient medium suitable for production of the polypeptide using methods known in the art. For example, the cell may be cultivated by shake flask cultivation, small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art (see, e.g., references for bacteria and yeast; Bennett, J. W. and LaSure, L., editors, *More Gene Manipulations in Fungi,* Academic Press, Calif., 1991). Suitable media are available from commercial suppliers or may be prepared according to published compositions (e.g., in catalogues of the American Type Culture Collection). If the polypeptide is secreted into the nutrient medium, the polypeptide can be recovered directly form the medium. If the polypeptide is not secreted, it is recovered from cell lysates.

The polypeptides may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide. The production of lipase activity can be determined by any method known in the art. In one method, one Lipase Unit (LU) is the amount of enzyme which liberates 1.0 $\mu$mol of titratable fatty acid per minute with tributyrin as substrate and gum arabic as an emulsifier at 30° C., pH 7.0 (phosphate buffer). Lipolytic enzyme activity in the absence of free $Ca^{++}$ in the range pH 1–10 is tested with a substrate emulsion of olive oil: 2% PVA solution (1:3) at 40° C. for 10 minutes, at a specified pH. At the end of the reaction, the reaction mixture is extracted by chloroform:methanol (1:1) at acidic conditions, and the fatty acid released during the reaction is measured by TLC-FID analysis (Iatroscan). One OPID unit (OPIDU) is taken as the release of 1.0 $\mu$mole of fatty acid per minute. In each test, 10 mM EDTA is used together with 200 mM of buffer (Tris-HCl buffer at pH 7 and 8, diethanol amine buffer at pH 8, 9 and 10).

The resulting polypeptide may be recovered by methods known in the art. For example, the polypeptide may be recovered from the nutrient medium by conventional procedures including, but not limited to, centrifugation, filtration, extraction, spray-drying, evaporation, or precipitation. The recovered polypeptide may then be further purified by a variety of chromatographic procedures, e.g., ion exchange chromatography, gel filtration chromatography, affinity chromatography, or the like.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing (IEF), differential solubility (e.g., ammonium sulfate precipitation), or extraction (see, e.g., *Protein Purification,* J. -C. Janson and Lars Ryden, editors, VCH Publishers, New York, 1989).

Uses

The recombinant polypeptides enoded by the nucleic acid sequences of the invention may be used in conventional applications of lipolytic enzyme, particularly at a high pH, e.g., in laundry and dishwashing detergents, institutional and industrial cleaning and leather processing.

The lipolytic enzymes of the invention can also be used for interesterification, for total hydrolysis of fats and oils, and in optical isomer resolution process.

The present invention is further described by the following examples which should not be construed as limiting the scope of the invention.

EXAMPLES

Example 1

Genomic DNA Extraction

*Absidia griseola* NN000987 (ATCC 20430), *Absidia sporophora-variabilis* NN102427 (ATCC 36019), *Absidia griseola* var. igushii NN000591 (ATCC 20431), *Absidia corymbifera* NN100062 (IFO 8084), and *Absidia blakesleana* NN100826 (NRRL 1304) were each grown in 25 ml of 0.5% yeast extract-2% glucose (YEG) medium for 24 hours at 32° C. and 250 rpm. Mycelia from each culture were then collected by filtration through Miracloth (Calbiochem, La Jolla, Calif.) and washed once with 25 ml of 10 mM Tris-0.1M EDTA (TE) buffer. Excess buffer was drained from the mycelia preparations which were subsequently frozen in liquid nitrogen. The frozen mycelia preparations were ground to a fine powder in an electric coffee grinder, and the powders were each added to a disposable plastic centrifuge tube containing 20 ml of TE buffer and 5 ml of 20% w/v sodium dodecylsulfate (SDS). The mixtures were gently inverted several times to ensure mixing, and extracted twice with an equal volume of phenol:chloroform:isoamyl alcohol (25:24:1 v/v/v). Sodium acetate (3M solution) was added to the extracted samples to a final concentration of 0.3M followed by 2.5 volumes of ice cold ethanol to precipitate the DNA. The tube were centrifuged at 15,000× g for 30 minutes to pellet the DNA. The DNA pellets were allowed to air-dry for 30 minutes before resuspension in 0.5 ml of TE buffer. DNase-free ribonuclease A was added to the resuspended DNA pellets to a concentration of 100 μg/ml and the mixtures were then incubated at 37° C. for 30 min. Proteinase K (200 μg/ml) was added and each tube was incubated an additional one hour at 37° C. Finally, each sample was extracted twice with phenol:chloroform:isoamyl alcohol (25:24:1 v/v/v) before precipitating the DNA with sodium acetate and ethanol. The DNA pellets were dried under vacuum, resuspended in TE buffer, and stored at 4° C.

Example 2

PCR Amplification of *Absidia griseola* NN000987 and *Absidia griseola* var. iguchii NN000591 Lipase Gene Segments Based on the amino acid sequences of the *Absidia griseola* NN000987 lipase and the *Absidia griseola* var. iguchii NN000591 lipase as disclosed by Gormsen et al., in Patent Application DK 95/00424 (the contents of which are incorporated herein by reference), the oligonucleotide primers shown below were synthesized with an Applied Biosystems Model 394 DNA/RNA Synthesizer, according to the manufacturer's instructions, to PCR amplify lipase gene fragments from *Absidia griseola* NN000987 and *Absidia griseola* var. iguchii NN000591 (Note: R=A or G, I=inosine, Y=T or C, H=A or T or C, and N=A or T or C or G):

1. Forward primer

Amino acid sequence: GluThrGluIleGlnAlaHisThrPhe (SEQ ID NO:11)

Oligonucleotide (+strand): 5'-GARACIGARATHCARGCICAYACITT-3'(SEQ ID NO:12)

2. Reverse primer

Amino acid sequence: ProProGlyAlaPheGlyPheLeu (SEQ ID NO:13)

Oligonucleotide (−strand): 5'-ARRAANCCRAAIGCNCCIGGNGG-3'(SEQ ID NO:14)

Amplification reactions (100 ml) were prepared using approximately 1 μg of *Absidia griseola* NNN000987 or *Absidia griseola* var. iguchii NN000591 genomic DNA as the template. Each reaction contained the following components: 1 μg of genomic DNA, 40 pmol of forward primer, 40 pmol of reverse primer, 200 mM each of dATP, dCTP, dGTP, and dTTP, 1×Taq polymerase buffer (Perkin-Elmer Corp., Branchburg, N.J.), and 5 Units of Taq polymerase (Perkin-Elmer Corp., Branchburg, N.J.). Sterile mineral oil (100 μl) was layered on top of each reaction mixture, and the reactions were incubated in a Perkin-Elmer Model 480 Thermal Cycler programmed as follows: Cycle 1—95° C. for 5 minutes, 45° C. for 2 minutes, and 67° C. for 5 minutes; Cycle 2—30°–95° C. for 2 minutes; 45° C. for 2 minutes, and 67° C. for 2 minutes; and Soak cycle at 4° C. The reaction products were isolated on a 1% low melting point agarose gel (Sigma Chemical Co., St. Louis, Mo.) and the major PCR product band from each reaction was excised from the gel and purified using β-agarase (New England Biolabs, Beveraly, Mass.) according to the manufacturer's instructions. The purified PCR products were subsequently cloned into a pCRII vector (Invitrogen, San Diego, Calif.) and the DNA sequences were determined using lac forward and reverse primers (New England BioLabs, Beverly, Mass.).

Lipase gene segments of approximately 8970 bp were amplified from *Absidia griseola* NN000987 and *Absidia griseola* var. iguchii NN000591 as shown in FIG. 1 with the lipase-specific PCR primers described above. DNA sequence analysis showed that the amplified gene segments encode portions of the corresponding Absidia lipase genes. In addition, the DNA sequence data confirmed that these two gene products are probably identical and share regions of homology with the *Rhizomuco miehei* lipase.

Example 3

Hybridization Analysis of Genomic DNA

Total cellular DNA samples prepared from the five Absidia strains described in Example 1 were analyzed by Southern hybridization (Maniatis et al., 1982, *Molecular Cloning, A Laboratory Manual,* Cold Spring Harbor Press, Cold Spring Harbor, N.Y.). Approximately 2–5 μg of each DNA sample was digested with EcoRI, Asp718I or EcoRI plus Asp718I and fractionated on a 1% agarose gel. The gel was photographed under short wavelength UV light and soaked for 15 minutes in 0.5M NaOH—1.5M NaCl followed by 15 minutes in 1.5M NaCl—1M Tris-HCl pH 8. DNA in the gel was transferred onto NytranÔ hybridization membrane (Schleicher & Schuell, Keene; N.H.) by capillary blotting in 20× SSPE (3M sodium chloride—0.2M sodium dibasic phosphate—0.02M disodium EDTA) according to Davis et al. (1980, *Advanced Bacterial Genetics, A Manual for Genetic Engineering,* Cold Spring Harbor Press, Cold Spring Harbor, N.J.). The DNA was cross-linked onto the membrane using a UV Stratalinker (Stratagene, La Jolla, Calif.); and the membrane was soaked for 2 hours in the following hybridization buffer at 45° C. with gentle agitation: 5× SSPE, 35% formamide (v/v), 0.3% SDS, and 20 mg/ml denatured and sheared salmon testes DNA. The lipase-specific probe fragment isolated from the *Absidia griseola* NN000987 PCR-clone described in Example 2 was radiolabeled by nick translation (Maniatis et al., 1982, supra) with [$^{32}$P]dCTP (Amersham, Arlington Heights, Ill.), denatured by adding NaOH to a final concentration of 0.1M, and added to the hybridization buffer at an activity of approximately 1×10$^6$ cpm per ml of buffer. The mixture was incubated overnight at 45° C. in a shaking water bath. Following incubation, the membranes were washed once in 0.2× SSPE with 0.1% SDS at 45° C. followed by two washes in 0.2× SSPE (no SDS) at the same temperature. The membranes were allowed to dry on paper towels for 15 minutes, then wrapped in Saran-Wrap™ and exposed to X-ray film overnight at −70° C. with intensifying screens (Kodak, Rochester, N.Y.).

Figure 2:
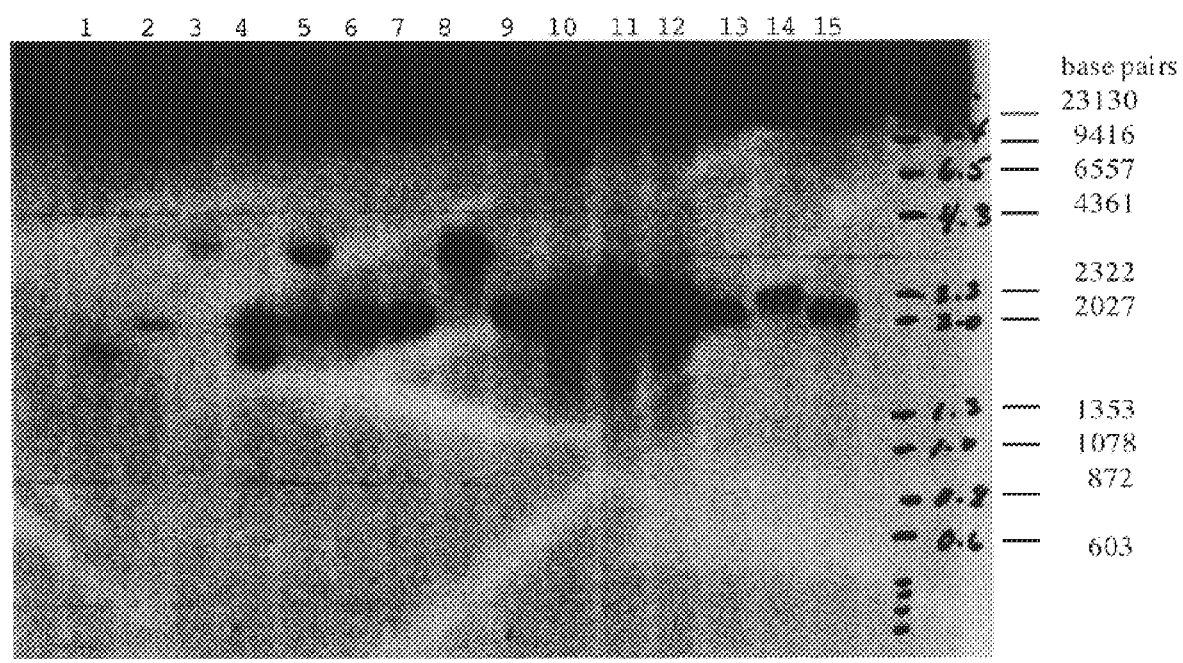
FIG. 2 shows an autoradiogram from Southern hybridization analysis of genomic DNA digests from several *Absidia* species probed with a radiolabeled lipase gene segment from *Absidia griseola*. The sizes of HindIII-digested lambda DNA and HaeIII-digested φX17RF-DNA size standards are indicated on the right side of the autoradiogram. Lanes 1–3: *Absidia sporophora-variabilis* DNA (EcoRI plus Asp718I, Asp718I and EcoRI, respectively); lanes 4–6:*Absidia corymbifera* DNA (EcoRI plus Asp718I, Asp718I and EcoRI, respectively); lanes 7–9:*Absidia blakesleeana* DNA (EcoRI plus Asp718I, Asp718I and EcoRI, respectively); lanes 10–12:*Absidia griseola* var. *iguchii* DNA (EcoRI plus Asp718I, Asp718I and EcoRI, respectively); and lanes 13–15:*Absidia griseola* DNA (EcoRI plus Asp718I, Asp718I and EcoRI, respectively).

Analysis of the total cellular DNA samples from each of the Absidia species by Southern blotting under conditions of moderate stringency using the PCR-derived lipase gene segment probe from *Absidia griseola* var. iguchii NN000591 demonstrated that the lipase genes of all the Absidia species tested cross-hybridized to the probe (FIG. 2). All the species tested also showed a single hybridization signal in the EcoRI digest of approximately 2.1 kb with the exception of *Absidia sporophora-variabilis* NN102427 which gave a hybridization signal with a 4 kb band. Furthermore, it appeared that all of the species tested contain a single copy of the corresponding lipase gene in their genomes.

Example 4
DNA Libraries and Identification of Lipase Clones

Enriched genomic DNA libraries were constructed in the bacteriophage cloning vector 1ZipLox (Life Technologies, Gaithersburg, Md.). First, total cellular DNA was digested with EcoRI and size-fractionated on 1% agarose gels. DNA fragments migrating in the size range corresponding to hybridization signals previously observed on Southern blots described in Example 3 were excised and eluted from the gel using Prep-a-Gene reagents (BioRad Laboratories, Hercules, Calif.). The approximate sizes of the DNA fragments in these fractions were as follows: 1.9–2.5 kb (*Absidia griseola* var. iguchii NN000591), 1.9–2.5 kb (*Absidia blakesleeana* NN100826), 1.9–2.5 kb (*Absidia corymbifera* NN100062) and 2.5–4.3 kb (*Absidia sporophora-variabilis* NN102427). the eluted DNA fragments were ligated with EcoRI-cleaved and dephosphorylated λZipLox vector arms (Life Technologies, Gaithersburg, Md.), and the ligation mixtures were packaged using commercial packaging extracts (Stratagene, La Jolla, Calif.). The packaged DNA libraries were plated and amplified in *Escherichia coli* Y1090ZL cells (Life Technologies, Gaithersburg, MD.). The titers of recombinant phage in each library ranged from 1.3—5.4×10$^5$ pfu/ml (background titers with no DNA were 1.7–2.0×10$^4$ pfu/ml). Approximately 15,000–30,000 plaques from each unamplified library were screened by plaque-hybridization using the lipase-specific PCR fragment from *Absidia griseola* NN000987 as the probe (Davis, et al., 1980, supra). Plaques, which gave strong hybridization signals with the probe, were purified twice in *E. coli* Y1090ZL cells and the lipase genes were subsequently excised from the λZipLox vector as pZL1-derivatives (D'Alessio et al., 1992, Focus® 14:76). The recombinant DNA segments were inserted within the phagemid pZL1 portion of the vector, and the phagemid harboring the cloned insert was recovered in the autonomously replicating pZL1 using in vivo excision by infection of *E. coli* DH10Bzip cells (Life Technologies, Gaithersburg, Md.). The lipase clones isolated in this manner were prepared for DNA sequence analysis using a Wizard 373 DNA purification kit (Promega, Madison, Wis.).

Example 5
DNA Sequence Analysis of Lipase Genes

DNA sequencing of the lipase clones described in Example 4 was performed with an Applied Biosystems Model 373A Automated DNA Sequencer (Applied Biosystems, Inc., Foster City, Calif.) on both strands using the primer walking technique with dye-terminator chemistry (Giesecke et al., 1992, *Journal of Virol. Methods* 38: 47–60). Oligonucleotide sequencing primers were synthesized on an Applied Biosystems Model 394 DNA/RNA Synthesizer according to the manufacturer's instructions.

The nucleotide sequences of the genes encoding the Absidia lipases are shown in FIGS. 3–6 (SEQ ID NOS:1, 3, 5, and 7). The assignment of introns within each gene was based on (a) known amino acid sequence data derived from peptide fragments (Boel et al., 1988, *Lipids* 23: 701–706), (b) alignment to the deduced amino acid sequence of *Rhizomucor miehei* lipase (SEQ ID NO:15)(Gurr et al., *In* Kinghorn, J. R. [ed], *Gene Structure in Eukaryotic Microbes*, pp. 93–139, IRL Press, Oxford), and (c) known consensus sequences for introns of filamentous fungi (von Heijne, 1984, *Journal of Molecular Biology* 173: 243–251).

In order to isolate a gene encoding the *Absidia reflexa* lipase, a strain of *Absidia reflexa* NN102427 (ATCC 44896) was grown on optimal medium with jojoba oil as an induction component. A cDNA library was prepared from this strain, and, using the *Absidia corymbifera* gene described above s a probe, a cDNA clone was identified by colony hybridization. The sequence of the *Absidia reflexa* gene is provided in FIG. 7 (SEQ ID NO:9). This lipase is approximately 99% identical with the *Absidia sporophora-variabilis* lipase.

Example 6
Comparison of the Lipase Genes from Absidia Species

The intron-exon organization among Absidia lipase genes is very similar in that all are composed of seven exons and six introns as shown in Table 1. The size of the exons 2 through 6 are strictly conserved. The first exon shows slight variability in size due to some variation in the region encoding the signal peptide and propeptide portions of the enzyme. In addition, the nucleotide sequence homology between corresponding exons is also very high with 85–97% identity. In contrast, the lengths of the introns varied, and with the exception of the *Absidia corymbifer* NN100062 and *Absidia sporophora-variabilis* NN102427 lipase genes, there is little sequence homology between corresponding introns. The 5' and 3' flanking sequences of the lipase genes also shows sequence divergence.

TABLE 1

Intron-exon organization of the lipase genes from several Absidia species.

| Species | Exon (length in bp) | | | | | | | Intron (length in bp) | | | | | |
|---|---|---|---|---|---|---|---|---|---|---|---|---|---|
| | 1 | 2 | 3 | 4 | 5 | 6 | 7 | 1 | 2 | 3 | 4 | 5 | 6 |
| A. griseola var. iguchii | 489 | 58 | 97 | 173 | 81 | 79 | 31 | 82 | 64 | 56 | 61 | 64 | 66 |
| A. blakesleeana | 492 | 58 | 97 | 173 | 81 | 79 | 31 | 75 | 52 | 57 | 60 | 64 | 67 |
| A. corymbifera | 495 | 58 | 97 | 173 | 81 | 79 | 31 | 61 | 62 | 54 | 55 | 53 | 59 |
| A. sporophora-variabilis | 495 | 58 | 97 | 173 | 81 | 79 | 31 | 61 | 62 | 54 | 57 | 53 | 59 |

Based on the deduced amino acid sequences (SEQ ID NOS:2, 4, 6, 8, and 10), a comparison of the biochemical and biophysical properties of the Absidia lipases is presented in Table 2. All four lipases are very similar in that all are synthesized as preproenzymes of 337–338 amino acids, comprising signal peptides of 17–21 amino acids, propeptides of 52–56 amino acids, and mature enzymes of 264–265 amino acids with molecular weights of approximately 29,000 for the non-glycosylated proteins. The calculated isoelectric points vary from 6.10 to 6.94 with the most alkaline being the lipase from Absidia sporophora-variabilis. These calculated isoelectric values are much lower than those observed experimentally on IEF gels (see Gormsen et al. in Patent Application DK 95/00424) probably as a result that not all charged residues are on the exposed three-dimensional surface of the protein.

From a phylogenetic standpoint, the Absidia lipases are most closely related to the lipases from other members of the Zygomycete class of fungi. Yeast, bacterial, and mammalian lipases as well as fungal cutinase appear to be very distantly related if at all.

Example 7
Expression of the Absidia corymbifera lipase gene

Figure 9:
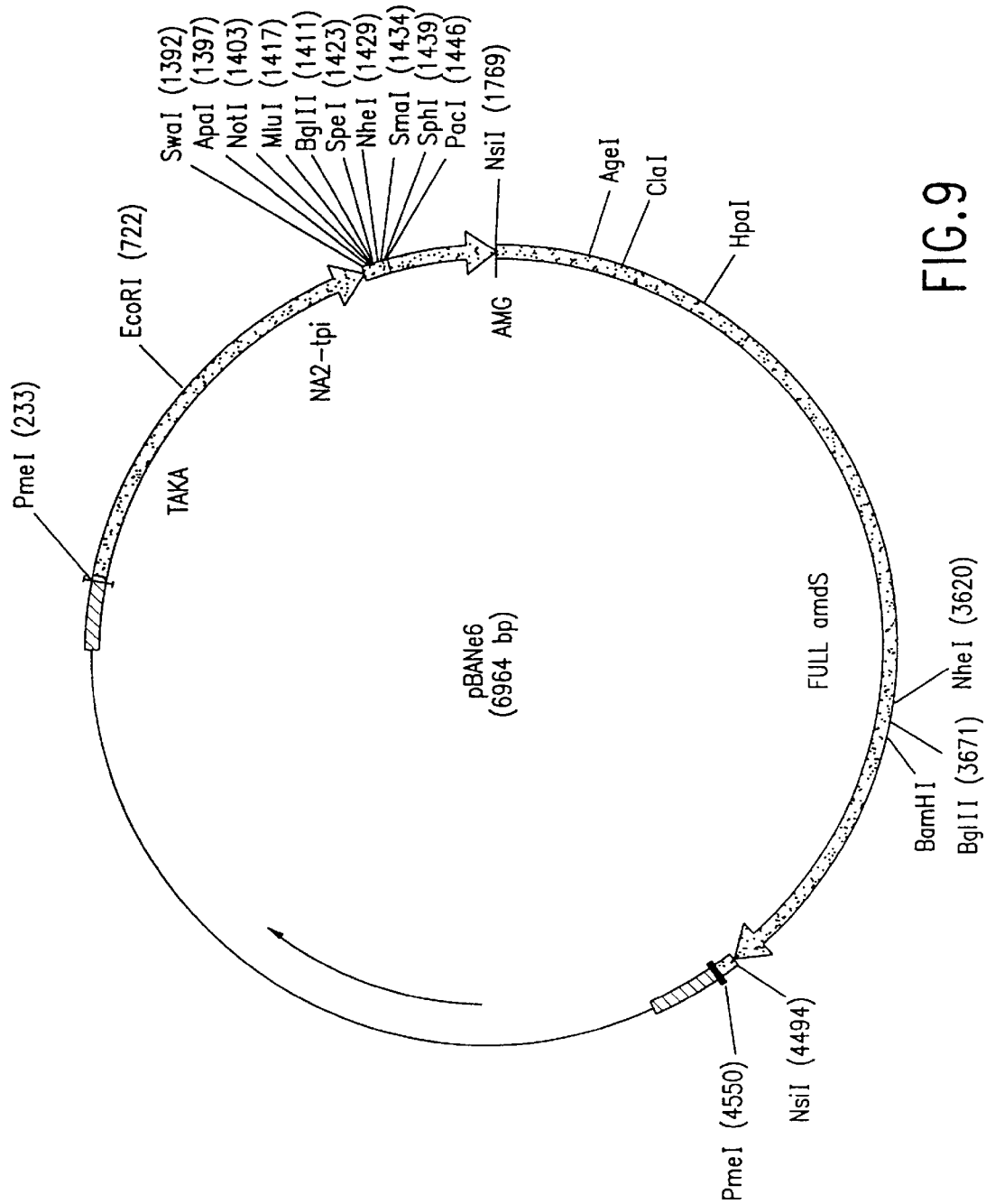
FIG. 9 shows a restriction map of pBANe6.

The clone and the nucleotide sequences of the Absidia corymbifera lipase gene described above were used for subcloning of the gene and expression in an Aspergillus host. PCR was used to subclone the lipase gene (without its own promoter) from the isolated genomic clone NL95A using primers designed from the nucleotide sequences. In order to facilitate the subcloning of the gene fragment into an expression vector designated pBNAe6 (FIG. 9), SwaI and PacI restriction enzyme sites, respectively, at the 5' and 3' end of the gene, were introduced. The vector pBANE6 contained the TAKA promoter, NA2-tpi leader, and AMG terminator as regulatory sequences. The plasmid also contained the Aspergillus nidulans amdS gene as a selectable marker for fungal transformations. The following primers were used for PCR amplification:

TABLE 2

Predicted biochemical and biophysical properties of from several Absidia species.

| Species | Preproform | Predicted signal peptide | Predicted propeptide | Mature lipase | Molecular weight | Calculated isoelectric point | Molar extinction coefficient | I A280 unit (mg/ml) |
|---|---|---|---|---|---|---|---|---|
| A. griseola var. iguchii | 337 aa | 18 aa | 54 aa | 264 aa | 29,028 | 6.45 | 27,580 | 1.05 |
| A. blakesleeana | 337 aa | 18 aa | 55 aa | 264 aa | 28,959 | 6.64 | 24,900 | 1.16 |
| A. corymbifera | 338 aa | 21 aa | 52 aa | 265 aa | 29,057 | 6.10 | 27,460 | 1.06 |
| A. sporophora-variabilis | 338 aa | 17 aa | 56 aa | 265 aa | 28,952 | 6.94 | 27,460 | 1.05 |

Figure 8B:
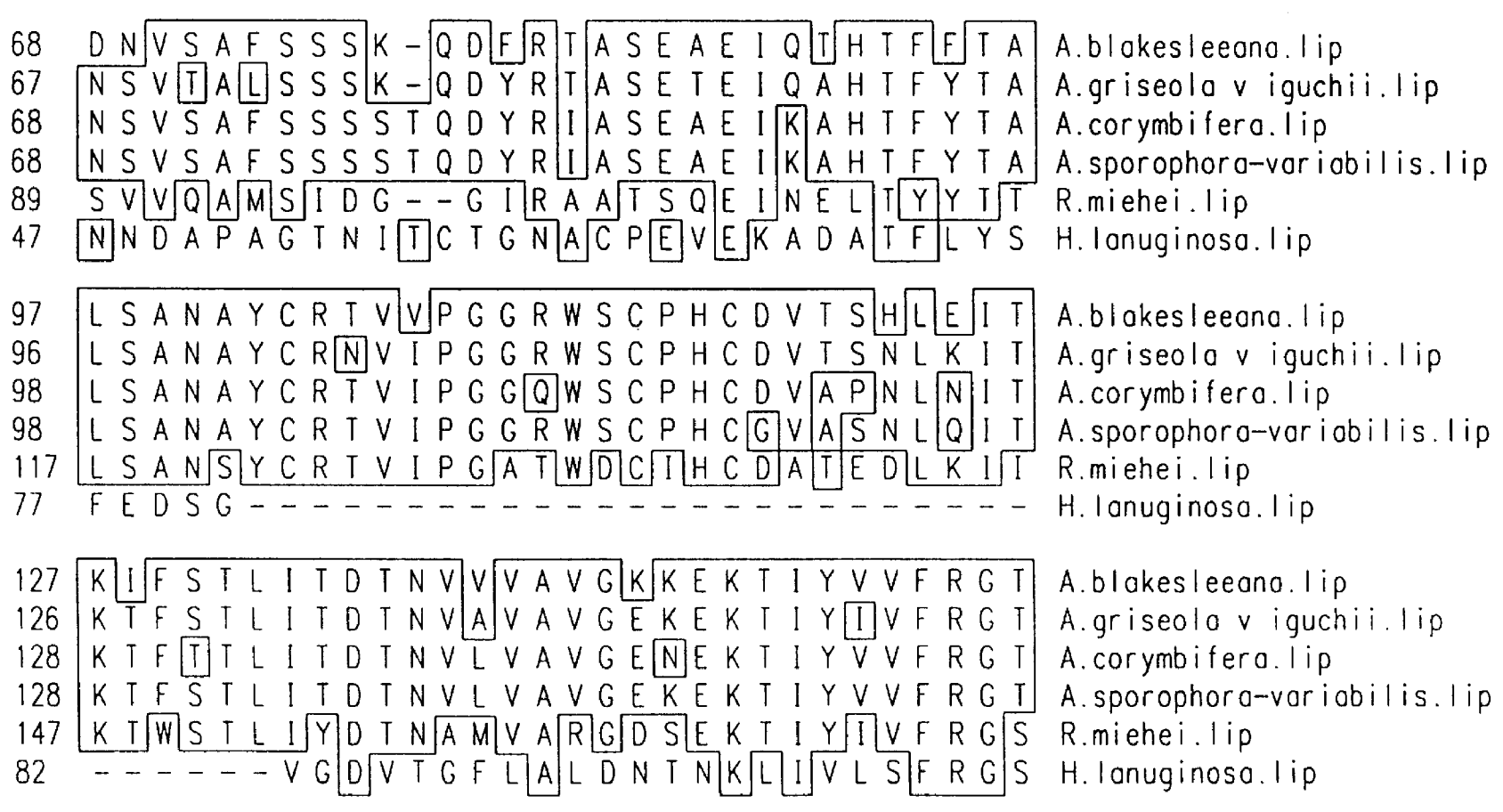
Figure 8C:
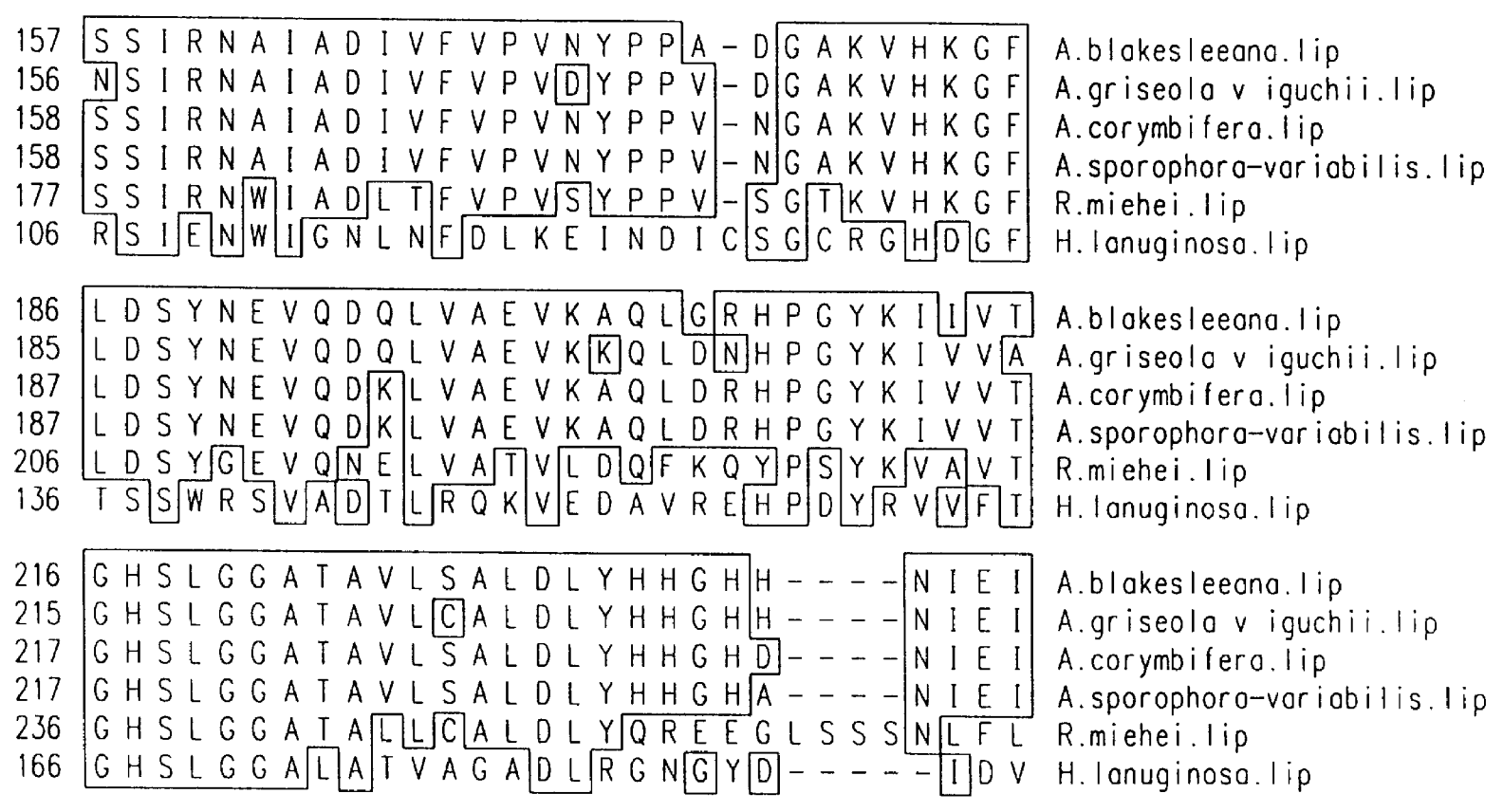

The Absidia lipases share extensive amino acid sequence homology between each other with 87–96% identity, and limited homology to Rhizomuco miehei lipase (SEQ ID NO:15) with 53–55% identity and Humicola lanuginosa lipase (SEQ ID NO:16) with 22–24% identity as shown in Table 3 and FIG. 8.

TABLE 3

Amino acid sequence similarity among lipases from Absidia species, R. miehei, and H. lanuginosa

| | | Percent Similarity | | | | | | |
|---|---|---|---|---|---|---|---|---|
| | | 1 | 2 | 3 | 4 | 5 | 6 | |
| Percent | 1 | — | 87.2 | 87.5 | 88.1 | 53.7 | 22.3 | 1 A. blakesleeana |
| Divergence | 2 | 11.9 | — | 86.3 | 87.2 | 54.8 | 22.7 | 2 A. griseola var. iguchii |
| | 3 | 11.6 | 11.9 | — | 96.4 | 53.3 | 23.7 | 3 A. corymbifera |
| | 4 | 11.0 | 11.0 | 3.6 | — | 53.3 | 24.1 | 4 A. sporophora-variabilis |
| | 5 | 41.6 | 40.5 | 41.9 | 41.9 | — | 23.7 | 5 R. miehei |
| | 6 | 70.6 | 70.9 | 70.0 | 70.0 | 68.8 | — | 6 Humicola lanuginosa |
| | | 1 | 2 | 3 | 4 | 5 | 6 | |

Forward Primer: 5'-CCCATTTAAATAT-GCGTTTTTATTCAGTAGTATCAT-3'(SEQ ID NO:17)
Reverse primer: 5'-CTCGGCTTAATTAAAATGGG-TTATAAGCAGAGACCAGTG-3'(SEQ ID NO:18)

Figure 10:
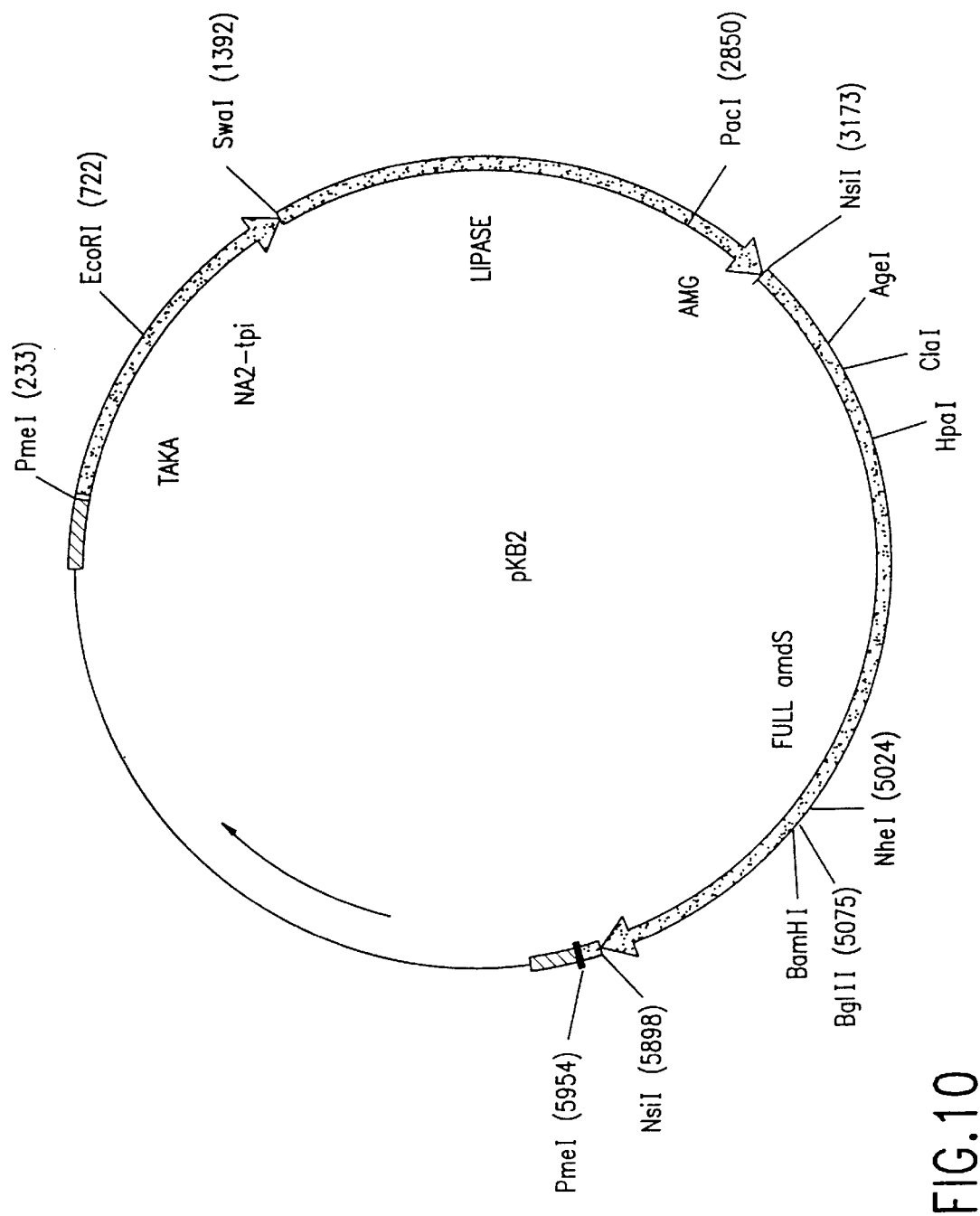
FIG. 10 shows a restriction map of pKB2.

PCR was performed using Pwo polymerase (Boehringer Mannheim, Indianapolis, Ind.) according to manufacturer's specifications. The PCR amplified product was gel isolated, cut with SwaI and PacI enzymes, and gel purified. The purified fragment was ligated to the pBANe6 vector (already cut with SwaI and PacI) to yield the plasmid pKB2 (FIG. 10) in which transcription of the lipase gene was under the control of the TAKA promoter. The plasmid pKB2 was transformed into E. coli DH5 cells. E. coli transformants containing the pKB2 plasmid were isolated and plasmid DNA was prepared for transformation and expression in Aspergillus.

Protoplasts were prepared from *Aspergillus oryzae* strain BANe3 in which the amdS gene of the host strain was deleted. Protoplast preparation and transformation were done as previously described (Christensen et al., supra). *Aspergillus oryzae* transformants expressing acetamidase were selected based on their ability to utilize acetamide as the sole nitrogen source. A total of 42 transformants were generated and spore purified twice on selective plates. The spore purified transformants were used for further analysis.

The transformants were screened for lipase expression by cultivation in shake flasks (25 ml medium in 125 ml flasks) using a medium containing 50 g of maltose, 2.0 g of $MgSO_4\cdot 7H_2O$, 10 g of $KH_2PO_4$, 2.0 g of citric acid, 10 g of yeast extract, 0.5 ml of trace metals solution, and 2.0 g of urea per liter. The trace metals solution was comprised of 14.3 g of $ZnSO_4\cdot 7H_2O$, 2.5 g of $CuSO_4\cdot 5H_2O$, 0.5 g of $NiCl_2\cdot 6H_2O$, 13.8 g of $FeSO_4\cdot 7H_2O$, 8.5 g of $MnSO_4\cdot H_2O$, and 3.0 g of citric acid per liter. The pH of the medium was adjusted to 6.5 before sterilization by autoclaving. Flasks were inoculated with freshly harvested spores and incubated in an incubator at 34° C. and 200 rpm. Cultures were assayed for lipase activity daily after 48 hours of cultivation. Since nothing was known about the suitable substrate for this lipase, enzyme activity was assayed by three methods: i) lipase plate assay using olive oil as the substrate, ii) colorimetrically using p-nitrophenylbutyrate as the substrate and iii) titration using tributyrin (triglyceride of butyric acid).

A lipase plate assay was performed using a plate medium that contained the following: 0.1M Tris pH 9.0, 0.1M $CaCl_2$, 1% Triton X-100, 0.5% olive oil, and 2.0% agarose. The medium was autoclaved and poured into 150 mm plates using 50–60 ml per plate. After solidification of the agarose, 15 wells per plate were made and 25 ml of the culture broth was added to each well. Culture broth from untransformed *Aspergillus oryzae* strain BANe3 was used as a control. The plates were incubate overnight at 37° C. The presence of lipase activity in the transformants was identified as clear zones around the well. Control wells loaded with culture broth from the untransformed strain did not show such clearing indicating the presence of lipase activity only in the transformants.

Lipase activity was also measured colorimetrically using p-nitrophenylbutyrate as a substrate. p-Nitrophenylbutyrate was prepared by adding 10 ml of this compound to 1.0 ml dimethylsulfoxide (DMSO) and 4.0 ml of 0.1M Tris pH 9.0 buffer. One hundred microliters of suitably diluted culture broth were added to each well. The reaction was started by adding 100 ml of the p-nitrophenylbutyrate substrate and the absorbance was measured at 405 nm for 3–5 min. The enzyme activity was calculated from a curve made with a known amount of *Humicola lanuginosa* lipase as the standard. The untransformed strain produced little or no activity while different transformants produced lipase after 48 hours of cultivation.

Lipase activity was further determined by titration based on the hydrolysis of tributyrin catalyzed by the lipase. The liberation of butyric acid was followed by alkaline titration in a pH-stat. The assay was performed on culture broths from selected transformants as well as from the untransformed control strain. The results showed that the untransformed control strain produced no lipase activity, while the transformants produced detectable lipase activity.

Example 8

Expression of the *Absidia sporophora-variabilis* Lipase Gene in *Aspergillus oryzae*.

Figure 11:
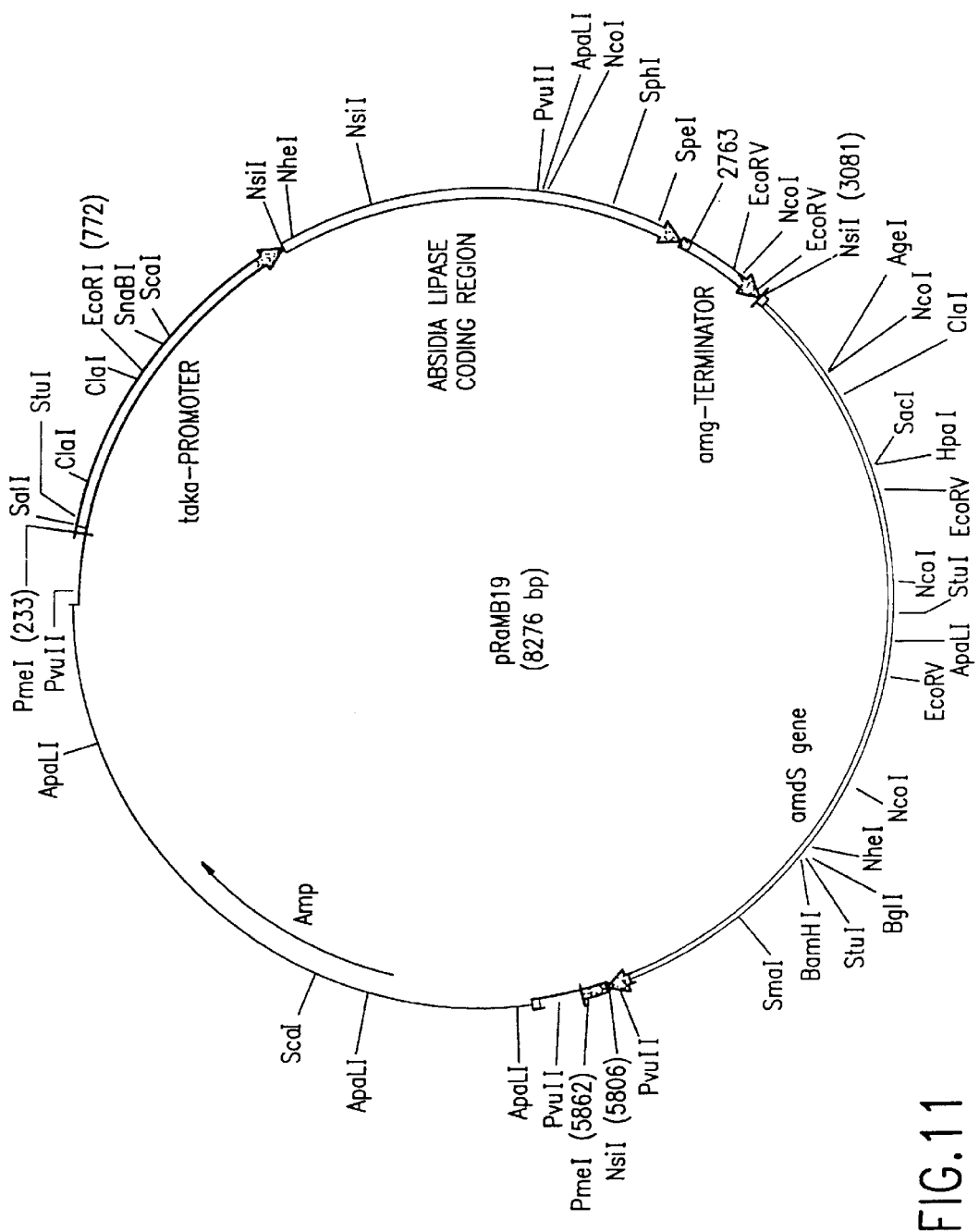
FIG. 11 shows a restriction map of pRamB19.

The coding region of the *A. sporophora-variabilis* lipase as amplified using the original genomic clone as the template for Pwo polymerase (Boehringer-Mannheim Biochemicals, Indianapolis, Ind.) in a PCR reaction which contained the following: 61 ml sterile water, 10 ml of diluted template DNA (ca. 5 ng/ml), 1 ml primer 1 (ca. 30 pmol: dATGATGCATTCTCATTTTGTAGTCTTATTG, SEQ ID NO:19) 1 ml primer 2 (ca. 25 pmol: dGCTTAA-TTAATTATAAACAGAGACGAGTGTTCATGTCAAG, SEQ ID NO:20), 16 ml dATP, dCTP, dGTP, and dTTP mix (200 mmol final concentration), 10 ml of Pwo buffer (10× solution; Boehringer-Mannheim Biochemicals), and 1 ml Pwo polymerase (5 units). Amplification conditions were as follows: First cycle at 95° C. for 5 minutes, 45° C. for 2 minutes, and 67° C. for 5 minutes; cycles 2 through 30 at 95° C. for 2 minutes, 45° C. for 1 minute, and 67° C. for 2 minutes; and a soak cycle at 4° C. The amplified lipase gene segment was digested with PacI and isolated by preparative agarose gel electrophoresis, excised and purified using Prep-a-Gene reagents (BioRad Laboratories, Hercules, Calif.). The purified fragment was ligated with pBANe6 which had been cleaved with SwaI and PacI to generate the lipase expression vector pRaMB19(FIG. 11).

pRaMB19 was subsequently used to transform an alkaline protease-deficient *Aspergillus oryzae* host JaL142 using standard methods (Christensen et al. 1988. *Bio/Technology* 1419–1422). Transformant colonies were purified twice through condiospores and tested for lipase expression by streaking on tributyrin agar plates containing 130 g of maltodextrin, 3 g of $MgSO_4\cdot 7H_2O$, 5 g of $KH_2PO_4$, 4 g of citric acid, 6 g of $K_2SO_4$, 0.5 ml of trace metals (described in Example 7), 5 g of yeast extract, 166 ml of 1M urea, 35.3 ml of 1M $NaNO_3$, 25 g of Noble agar, and 10 g of tributyrin pH 4.5 per liter. After a 48 hour incubation at 30° C., 80 of 84 transformants showed distinct clearing zones on the tributyrin agar plates indicating production of extracellular lipase activity. Ten of these transformants were further tested in shake flask cultures of MY50 medium containing 50 g of maltodextrin, 2 g of $MgSO_7\cdot 7H_2O$, 10 g of $KH_2PO_4$, 2 g of citric acid, 2 g of $K_2SO_4$, 0.5 ml of trace metals solution, 10 g of yeast extract, 2 g of urea pH 6.0 per liter. After incubating the shake flask cultures at 37° C. for 48 hours, culture filtrates from each were assayed for extracellular lipase activity using p-nitrophenyl butyrate as the substrate as described in Example 7. Cultures of untransformed control cells produced no detectable lipase activity, whereas the pRaMB19 transformants produced detectable lipase activity.

Deposit of Biological Materials

The following biological materials have been deposited under the terms of the Budapest Treat with the Agricultural Research Service Patent Culture Collection, Northern Regional Research Center, 1814 University Street, Peoria, Ill., 61604 on Jan. 18, 1996, and given the following accession numbers.

| Deposit | Accession Number |
|---|---|
| E. coli DH10B (pZL-NL1) - Absidia blakesleeana | NRRL B-21520 |
| E. coli DH10B (pZL-NL61) - Absidia corymbifera | NRRL B-21521 |
| E. coli DH10B (pZL-NL95) - Absidia griseola-iguchii | NRRL B-21522 |
| E. coli DH10B (pZL-NL124) - Absidia sporophora-variabilis | NRRL B-21523 |

What is claimed is:

1. An isolated nucleic acid sequence encoding a polypeptide having lipase activity selected from the group consisting of:
   (a) a nucleic acid sequence which encodes a polypeptide having lipase activity with the amino acid sequence of SEQ ID NO:2, SEQ ID NO:4, SEQ ID NO:6, SEQ NO:8, or SEQ ID NO:10;
   (b) a nucleic acid sequence obtained from an ABsidia strain which hybridizes under low stringency conditions to (i) the nucleic acid sequence of SEQ ID NO:1, SEQ ID NO:3, SEQ ID NO:5, SEQ ID NO:7, or SEQ ID NO:9 or (ii) its complementary strand;
   (c) an allelic form of (a) or (b); and
   (d) a fragment of (a), (b), or (c) which retains lipase activity.

2. The nucleic acid sequence of claim 1, which encodes a polypeptide with the amino acid sequence of SEQ ID NO:2.

3. The nucleic acid sequence of claim 2, which is SEQ ID NO:1.

4. The nucleic acid sequence of claim 1, wherein the nucleic acid sequence is contained in pZL-NL95 contained in *Escherichia coli* NRRL-B 21522.

5. The nucleic acid sequence of claim 1, which encodes a polypeptide with the amino acid sequence of SEQ ID NO:4.

6. The nucleic acid sequence of claim 5, which is SEQ ID NO:3.

7. The nucleic acid sequence of claim 1, wherein the nucleic acid sequence is contained in pZL-NL1 in *Escherichia coli* NRRL-B 21510.

8. The nucleic acid sequence of claim 1, which encodes a polypeptice with the amino acid sequence of SEQ ID NO:6.

9. The nucleic acid sequence of claim 8 which is SEQ ID NO:5.

10. The nucleic acid sequence of claim 1, wherein the nucleic acid sequence is contained in pZL-NL61 contained in *Escherichia coli* NRRL-B-21521.

11. The nucleic acid sequence of claim 1, which encodes a polypeptide with the amino acid sequence of SEQ ID NO:8.

12. The nucleic acid sequence of claim 11, which is SEQ ID NO:7.

13. The nucleic acid sequence of claim 1, wherein the nucleic acid sequence is contained in pZL-NL124 contained in *Escherichia coli* NRRL-B-21523.

14. The nucleic acid sequence of claim 1, which encodes a polypeptide with the amino acid sequence of SEQ ID NO:10.

15. The nucleic acid sequence of claim 14, which is SEQ ID NO:9.

16. The nucleic acid sequence of claim 1, wherein the nucleic acid sequence hybridizes under low stringency conditions to the nucleic acid sequence of SEQ ID NO:1 or its complementary strand.

17. The nucleic acid sequence of claim 16, wherein the nucleic acid sequence is capable of hybridizing under medium stringency conditions to the nucleic acid sequence of SEQ ID NO:1 or its complementary strand.

18. The nucleic acid sequence of claim 17, wherein the nucleic acid sequence hybridizes under high stringency conditions to the nucleic acid sequence of SEQ ID NO:1 or its complementary strand.

19. The nucleic acid sequence of claim 1, wherein the nucleic acid sequence hybridizes under low stringency conditions to (i) the nucleic acid sequence of SEQ ID NO:3 or its complementary strand.

20. The nucleic acid sequence of claim 19, wherein the nucleic acid sequence hybridizes under medium stringency conditions to (i) the nucleic acid sequence of SEQ ID NO:3 or its complementary strand.

21. The nucleic acid sequence of claim 20, wherein the nucleic acid sequence hybridizes under high stringency conditions to (i) the nucleic acid sequence of SEQ ID NO:3 or its complementary strand.

22. The nucleic acid sequence of claim 1, wherein the nucleic acid sequence hybridizes under low stringency to the nucleic acid sequence of SEQ ID NO:5 or it complementary strand.

23. The nucleic acid sequence of claim 22, wherein the nucleic acid sequence hybridizes under medium stringency conditions to the nucleic acid sequence of SEQ ID NO:5 or its complementary strand.

24. The nucleic acid sequence of claim 23, wherein the nucleic acid sequence hybridizes under high stringency conditions to the nucleic acid sequence of SEQ ID NO:5 or its complementary strand.

25. The nucleic acid sequence of claim 1, wherein the nucleic acid sequence hybridizes under low stringency conditions to the nucleic acid sequence of SEQ ID NO:7 or its complementary strand.

26. The nucleic acid sequence of claim 25, wherein the nucleic acid sequence hybridizes under medium stringency conditions to the nucleic acid sequence of SEQ ID NO:7 or its complementary strand.

27. The nucleic acid sequence of claim 26, wherein the nucleic acid sequence hubridizes under high stringency conditions to the nucleic acid sequence of SEQ ID NO:7 or its complementary strand.

28. The nucleic acid sequence of claim 1, wherein the nucleic acid sequence hybridizes under low stringency conditions to the nucleic acid sequence of SEQ ID NO:9 or its complementary strand.

29. The nucleic acid sequence of claim 28, wherein the nucleic acid sequence hybridizes under medium stringency conditions to the nucleic acid sequence of SEQ ID NO:9 or its complementary strand.

30. The nucleic acid sequence of claim 29, wherein the nucleic acid sequence hybridizes under high stringency conditions to the nucleic acid sequence of SEQ ID NO:9 or its complementary strand.

31. The nucleic acid sequence of claim 1, wherein the nucleic acid sequence encodes a polypeptide having lipase activity obtained from *Absidia blakesleeana*.

32. The nucleic acid sequence of claim 1, wherein the nucleic acid sequence encodes a polypeptide having lipase activity obtained from *Absidia corymbifera*.

33. The nucleic acid sequence of claim 1, wherein the nucleic acid sequence encodes a polypeptide having lipase activity obtained from *Absidia griseola*.

34. The nucleic acid sequence of claim 1, wherein the nucleic acid sequence encodes a polypeptide having lipase activity obtained from *Absidia griseola var. iguchii*.

35. The nucleic acid sequence of claim 1, wherein the nucleic acid sequence encodes a polypeptide having lipase activity obtained from *Absidia reflexa*.

36. The nucleic acid sequence of claim 1, wherein the nucleic acid sequence encodes a polypeptide having lipase acitivity obtained from *Absidia sporophora-variabilis*.

37. A nucleic acid construct comprising the nucleic acid sequence of claim 1 operably linked to one or more control sequences for directing the expression of the polypeptide in a suitable expression host.

38. A recombinant expression vector comprising the nucleic acid construct of claim 37, a promoter, and transcriptional and translational stop signals.

39. A recombinant host cell comprising the nucleic acid construct of claim 37.

40. A method of producing a polypeptide having lipase activity, comprising: (a) cultivating the host cell of claim 39 under conditions conducive to expression of the polypeptide; and (b) recovering the polypeptide.

* * * * *

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
        ( A ) LENGTH: 2168 base pairs
        ( B ) TYPE: nucleic acid
        ( C ) STRANDEDNESS: single
        ( D ) TOPOLOGY: linear ( i i ) MOLECULE TYPE: Genomic DNA ( x i ) SEQUENCE DESCRIPTION: SEQ ID NO:1:

```
GAATTCTAAT  ATAGGCACGC  TTTCCCATAT  AGTGGTTATA  CCGACCCCAG  GATTCATGTA    60
GCATGGTTTC  ACTTGCCATT  GTCAATGGAA  TGTTTATATT  TCCTTCATAA  TCGTGCTCGG   120
TGATGCATGC  ACGTTTGATG  TACCACAGAT  TATGTCAGAC  AAAAATGTGG  AGCAGCAATG   180
AATAGCAAAC  CATTGACCAA  AAAAGAGCAA  TTACTATGCA  CATTAGCATG  AGCGTGGTGC   240
ATATCCTGCA  TTTTCCCCAC  GCACAAGAGA  GATCTTTATT  TTTCCTTTGT  TACACGCACT   300
TTTGAAGCTA  TTGACTCTCG  TTGGTTCGCG  AGAACGGGAT  GTTGAGATAT  CTCGAGAGTG   360
AGAGAAAGAG  AGTTGGGGGC  AAAGCGGAAG  CTGATGTGAA  AAAGGGACCG  ATCGTCATCG   420
TTCATTCCTA  GCTCTATAAA  AAGGTAGCTC  TAATCCTTGT  CGGCAAAAGC  TGCTGTGTTC   480
TTGACAAACG  ATGCGTTTTT  ATTCAGTAGT  ATCATTGCTA  GCGGTATCCA  TCTGCACGTA   540
TGGTGTATCG  GGTGTGCCGG  TGCAAATTGG  TCCACGCGAC  AAGAGCTATG  TCCCTGAACA   600
ATATCCTCTG  AAAATGAATG  GTCCTTTGCC  TGAAGGTGTA  AGCGTCATCC  AGGGTTATTG   660
TGAAAACTGT  ACCATGTATC  CCGAAGAAAA  CAGCGTAACT  GCACTCTCAT  CGTCCAAACA   720
AGATTACCGT  ACAGCAAGCG  AGACTGAGAT  CCAGGCACAT  ACATTTTACA  CAGCGTTGTC   780
AGCCAATGCA  TATTGCAGAA  ATGTGATCCC  TGGTGGTCGT  TGGAGCTGCC  CTCACTGCGA   840
TGTCACATCC  AACTTGAAGA  TCACCAAGAC  TTTTAGCACG  TTAATCACTG  ATACCAACGT   900
CGCTGTTGCT  GTTGGCGAAA  AGGAGAAGAC  CATCTATATT  GTTTTCCGTG  GTACAAACTC   960
AATTCGCAAC  GCCATTGCGG  TAGGTTATTA  ACCCCAACAA  CAAGTATACT  ACTTGGCTTG  1020
TCAGCCTTCG  CTCATCATAT  ACATTGTCAT  TTTTTATATA  GGATATTGTC  TTTGTACCAG  1080
TGGATTATCC  ACCTGTTGAT  GGGGCCAAAG  TACACAAAGG  TATGTGCTAA  TCACGTGTCA  1140
TGTCATTAAA  TAATGCTCAA  CAAGTTGGTT  GTTTATTACA  CAGGATTCCT  TGATAGCTAT  1200
AATGAGGTCC  AAGATCAACT  TGTAGCCGAG  GTCAAAAAAC  AGCTTGATAA  CCATCCAGGA  1260
TACAAGATCG  TTGTCGCTGG  GTAAACGATT  GAAAACAGAA  CGCGGATGGC  ACGTGACTAA  1320
TTGGGTGTCA  TTGTAGGCAT  TCGTTGGGTG  GTGCAACAGC  CGTTCTTTGT  GCACTTGACC  1380
```

-continued

```
TTTATCACCA TGGCCACCAC AATATTGAAA TCTATACTCA AGGCCAGCCT CGTGTGGGAA    1440
CACCTGCATT TGCAAAGTAT GTGATTGGCA CCAAGATTCC ATACCAACGT CTTGTCAATG    1500
AGCGAGACAG TAAGTGCATT GCGACGACAT GTCTTTTTTC TCTGCCGCCT ACTAATGTTT    1560
GTATGTATAG TCGTTCCTCA CCTTCCACCT GGTGCTTTTG GTTTCCTACA TGCCGGCGAA    1620
GAGTTTTGGA TTATGAAAGA CAGCTCGTTG CGTAAGTAGT GTTGTTGCTT GGAAACGCTG    1680
AATATGGAAT ACTCATTGCA TGATATATTG AATAGGCGTA TGTCCTAATG GCATTGAGAC    1740
GGACGACTGC AGCAACTCCA TTGTTCCTTT CACCAGTGTC ATTGATCATT TAAGGTGAGT    1800
AGATTTGTCT ATATGAGATG ATCGTTTACA CAATTAACAT GTTTGGTCGG TCGAATATAG    1860
CTATCTTGAC ATGAACACTG GTCTTTGTTT ATAACCCATT CCTCTTAATG TAACCATGTA    1920
ATCGTAAATA TCCCTCATCC TTCAATATAA CAGAGCTATT AACATACTTT GTACAAAACC    1980
AATCCAATGG CTTTTATTAC GTGATGATGA ATAACCAAGA GTAATTAACG AGTTAGTCG     2040
AAAAGACCGA AGCCCATATC CTCATCAGAT TCCTCAGGCT CTTCTTCCTT GGCTTCTTCC    2100
TTCTTCTCTT CACCGGCAGC AGCGGGAGCG GCAGCAACGA CGAAAGCATC AGGGTTCTCC    2160
AAGAATTC                                                            2168
```

( 2 ) INFORMATION FOR SEQ ID NO:2:

( i ) SEQUENCE CHARACTERISTICS:
        ( A ) LENGTH: 336 amino acids
        ( B ) TYPE: amino acid
        ( C ) STRANDEDNESS: single
        ( D ) TOPOLOGY: linear ( i i ) MOLECULE TYPE: protein ( v ) FRAGMENT TYPE: internal ( x i ) SEQUENCE DESCRIPTION: SEQ ID NO:2:

```
Met Arg Phe Tyr Ser Val Val Ser Leu Leu Ala Val Ser Ile Cys Thr
 1               5                  10                  15

Tyr Gly Val Ser Gly Val Pro Val Gln Ile Gly Pro Arg Asp Lys Ser
            20                  25                  30

Tyr Val Pro Glu Gln Tyr Pro Leu Lys Met Asn Gly Pro Leu Pro Glu
        35                  40                  45

Gly Val Ser Val Ile Gln Gly Tyr Cys Glu Asn Cys Thr Met Tyr Pro
    50                  55                  60

Glu Glu Asn Ser Val Thr Ala Leu Ser Ser Ser Lys Gln Asp Tyr Arg
65                  70                  75                  80

Thr Ala Ser Glu Thr Glu Ile Gln Ala His Thr Phe Tyr Thr Ala Leu
                85                  90                  95

Ser Ala Asn Ala Tyr Cys Arg Asn Val Ile Pro Gly Gly Arg Trp Ser
            100                 105                 110

Cys Pro His Cys Asp Val Thr Ser Asn Leu Lys Ile Thr Lys Thr Phe
        115                 120                 125

Ser Thr Leu Ile Thr Asp Thr Asn Val Ala Val Ala Val Gly Glu Lys
    130                 135                 140

Glu Lys Thr Ile Tyr Ile Val Phe Arg Gly Thr Asn Ser Ile Arg Asn
145                 150                 155                 160

Ala Ile Ala Asp Ile Val Phe Val Pro Val Asp Tyr Pro Pro Val Asp
                165                 170                 175

Gly Ala Lys Val His Lys Gly Phe Leu Asp Ser Tyr Asn Glu Val Gln
            180                 185                 190

Asp Gln Leu Val Ala Glu Val Lys Lys Gln Leu Asp Asn His Pro Gly
```

|     | 195 |     |     |     |     | 200 |     |     |     |     | 205 |     |     |     |
| --- | --- | --- | --- | --- | --- | --- | --- | --- | --- | --- | --- | --- | --- | --- |
| Tyr | Lys 210 | Ile | Val | Val | Ala | Gly 215 | His | Ser | Leu | Gly | Gly 220 | Ala | Thr | Ala | Val |
| Leu 225 | Cys | Ala | Leu | Asp | Leu 230 | Tyr | His | His | Gly | His 235 | His | Asn | Ile | Glu | Ile 240 |
| Tyr | Thr | Gln | Gly | Gln 245 | Pro | Arg | Val | Gly | Thr 250 | Pro | Ala | Phe | Ala | Lys 255 | Tyr |
| Val | Ile | Gly | Thr 260 | Lys | Ile | Pro | Tyr | Gln 265 | Arg | Leu | Val | Asn | Glu 270 | Arg | Asp |
| Ile | Val | Pro 275 | His | Leu | Pro | Pro | Gly 280 | Ala | Phe | Gly | Phe | Leu 285 | His | Ala | Gly |
| Glu | Glu 290 | Phe | Trp | Ile | Met | Lys 295 | Asp | Ser | Ser | Leu | Arg 300 | Val | Cys | Pro | Asn |
| Gly 305 | Ile | Glu | Thr | Asp | Asp 310 | Cys | Ser | Asn | Ser | Ile 315 | Val | Pro | Phe | Thr | Ser 320 |
| Val | Ile | Asp | His | Leu 325 | Ser | Tyr | Leu | Asp | Met 330 | Asn | Thr | Gly | Leu | Cys 335 | Leu |

( 2 ) INFORMATION FOR SEQ ID NO:3:

( i ) SEQUENCE CHARACTERISTICS:
        ( A ) LENGTH: 2149 base pairs
        ( B ) TYPE: nucleic acid
        ( C ) STRANDEDNESS: single
        ( D ) TOPOLOGY: linear ( i i ) MOLECULE TYPE: Genomic DNA ( x i ) SEQUENCE DESCRIPTION: SEQ ID NO:3:

| GAATTCTAAT | ATAAGCACAC | TTTCCTATAT | GGCGATTAAA | CCGACACAGC | ATTCATAGCA | 60 |
| --- | --- | --- | --- | --- | --- | --- |
| TGGTTCCACT | TGGTCAATGT | CAATGGAATG | TTTATACTTC | TTTGATTAGT | TAATCGTGAT | 120 |
| CGGTGTTGCA | TGCACAATTG | ATGTGTCACA | GATTATGTCA | GACAAATGTG | AAGCAGCAAT | 180 |
| TAATAGCAAA | CCTTTCACCA | AAAGAGAACA | ATTACTATGC | ACATTAGCAT | GAGTGTGCAT | 240 |
| ATAATGCATT | TTTCCCCACG | CACAAGAGCG | AGATCTTTAT | TTTTCCTTTG | TTACACGCAC | 300 |
| TTTGGTAGCT | ATTGACTCTC | GTTGGTTCGC | GAGAACGGGA | TGAGATATTG | AGAGAGTTGG | 360 |
| GGGCAAAGCG | GAAGCTGATG | TGGAAAAAGG | GACCGATCAC | CATCTGTCGT | TCTTGGCTCT | 420 |
| ATATAAAAGT | AGCTCTCATT | TTGTCGCCAA | AAAGTGGCTG | TGTTCTTGAC | AAGCAATAAT | 480 |
| GCACTCTTAT | ATTCTAGTAT | TGCTGTTAGC | AGTATTCATC | TGCACATCTA | GTGTACTGGG | 540 |
| TGTGCCAATG | CAAATTGACC | AGCGCGACAA | GAAGAGCTAT | GTTCCTGAAC | AATATCCTCT | 600 |
| GAAAATGAAC | GGTCCTTTGC | CTGAAGGTGT | AAGCAAAATC | CAAGGCTATT | GTGAGAACTG | 660 |
| TACCATGTAT | CCTGAAGAAG | ATAACGTGTC | GGCATTCTCA | TCATCCAAAC | AAGACTTTCG | 720 |
| TACTGCAAGT | GAAGCTGAGA | TCCAGACACA | TACATTCTTT | ACAGCGTTGT | CAGCCAATGC | 780 |
| ATATTGCAGA | ACTGTGGTTC | CTGGTGGTCG | ATGGAGCTGT | CCCCACTGCG | ATGTCACATC | 840 |
| CCACTTGGAA | ATCACCAAGA | TTTTTAGCAC | ATTGATCACA | GATACCAATG | TTGTTGTTGC | 900 |
| TGTTGGCAAA | AAGGAGAAAA | CCATCTATGT | TGTTTTTCGT | GGTACAAGCT | CAATTCGCAA | 960 |
| CGCCATTGCT | GTAAGTTAAA | AACCCCTTAC | AAGCATAACA | GTTGTCAGCC | ACTTGCTCAT | 1020 |
| TATATTTATT | GTGTATTTCT | CATAGGATAT | TGTCTTTGTT | CCAGTGAATT | ATCCACCTGC | 1080 |
| TGATGGTGCC | AAAGTACACA | AAGGTACGTG | CTGATCACGT | GCATGTATTT | GGAACTCAAT | 1140 |
| ATGTTCTGTA | TGCAGGATTC | CTGGATAGCT | ATAACGAAGT | CCAAGATCAA | CTTGTCGCCG | 1200 |
| AAGTCAAGGC | ACAACTCGGT | CGTCATCCAG | GATACAAGAT | CATTGTCACT | GGGTAACACT | 1260 |

-continued

```
TGGAAAAAAG AAAGACACGG ATGGCACGTG ACTAAATGTG TCATTGTAGG CATTCGTTGG    1320

GTGGTGCAAC AGCTGTTCTC AGTGCACTTG ATCTTTATCA CCATGGTCAT CACAATATTG    1380

AAATTTACAC CCAAGGTCAA CCACGAGTGG GTACACCAGC ATTTGCAAAT TATGTGATTG    1440

GCACCAAGAT CCCATATCAG CGTCTTGTCA ATGAGCGTGA CAGTAAGTAT CTATGAACAA    1500

TGGGTTTCGT TGTCGACCCA TTAAATGATA TATTATGTAT AGTCGTTCCT CATCTTCCAC    1560

CTGGAGCTTT TGGTTTCCTA CATGCTGGTG AAGAGTTTTG GATCATGAAA GACAACTCAT    1620

TGCGTAAGTA TTGTCATGAG AAAGTTGAAT ATATGATTAC TCATTTATA TAAAACATAT     1680

CAAATAGGGG TATGTCCAAA TGGTATTGAG ACTGATGACT GTAGCAATTC CATTGTCCCT    1740

TTCACTAGTG TCATTGATCA TTTAAGGTAC GCACTTTGAT TTATTATATC GATCATTCAT    1800

CCAAGAATTA ACATATGGAA TCGAATCATC TAGCTATCTT GATATGAACA CTGGTCTCTG    1860

TTTATAATAT TTAGTATCGT TCTCTCATTC AATCTAATCT TGTCATACAA TCGTAAATAT    1920

CAATAAAGAA ACAGGGTAAA ATGAATGTTT TGTACAAAAC CGATTGAATG GCTTTTATTA    1980

TGAGATGAAG GATAACCAAG TGATATTAAC GAGTTTAGTC GAAAAGACCG AAGCCCATAT    2040

CCTCATCAGA TTCCTCAGCT TCTTCTTCCT TAGCTTCTTC CTTCTTTTCC TCACCACCAG    2100

CAACGGGAGC GGCAGCAACA ACGAAAGCAT CAGGGTTCTC CAAGAATTC                2149
```

( 2 ) INFORMATION FOR SEQ ID NO:4:

( i ) SEQUENCE CHARACTERISTICS:
        ( A ) LENGTH: 336 amino acids
        ( B ) TYPE: amino acid
        ( C ) STRANDEDNESS: single
        ( D ) TOPOLOGY: linear ( i i ) MOLECULE TYPE: protein ( v ) FRAGMENT TYPE: internal ( x i ) SEQUENCE DESCRIPTION: SEQ ID NO:4:

```
Met His Ser Tyr Ile Leu Val Leu Leu Leu Ala Val Phe Ile Cys Thr
 1               5                  10                  15

Ser Ser Val Leu Gly Val Pro Met Gln Ile Asp Gln Arg Asp Lys Lys
            20                  25                  30

Ser Tyr Val Pro Glu Gln Tyr Pro Leu Lys Met Asn Gly Pro Leu Pro
        35                  40                  45

Glu Gly Val Ser Lys Ile Gln Gly Tyr Cys Glu Asn Cys Thr Met Tyr
    50                  55                  60

Pro Glu Glu Asp Asn Val Ser Ala Phe Ser Ser Lys Gln Asp Phe
65                  70                  75                  80

Arg Thr Ala Ser Glu Ala Glu Ile Gln Thr His Thr Phe Phe Thr Ala
                85                  90                  95

Leu Ser Ala Asn Ala Tyr Cys Arg Thr Val Val Pro Gly Gly Arg Trp
            100                 105                 110

Ser Cys Pro His Cys Asp Val Thr Ser His Leu Glu Ile Thr Lys Ile
            115                 120                 125

Phe Ser Thr Leu Ile Thr Asp Thr Asn Val Val Val Ala Val Gly Lys
    130                 135                 140

Lys Glu Lys Thr Ile Tyr Val Val Phe Arg Gly Thr Ser Ser Ile Arg
145                 150                 155                 160

Asn Ala Ile Ala Asp Ile Val Phe Val Pro Val Asn Tyr Pro Pro Ala
                165                 170                 175

Asp Gly Ala Lys Val His Lys Gly Phe Leu Asp Ser Tyr Asn Glu Val
```

|     |     |     |     |     | 180 |     |     |     |     | 185 |     |     |     |     | 190 |     |     |
| --- | --- | --- | --- | --- | --- | --- | --- | --- | --- | --- | --- | --- | --- | --- | --- | --- | --- |
| Gln | Asp | Gln | Leu | Val | Ala | Glu | Val | Lys | Ala | Gln | Leu | Gly | Arg | His | Pro |
|     |     | 195 |     |     |     |     | 200 |     |     |     |     | 205 |     |     |     |
| Gly | Tyr | Lys | Ile | Ile | Val | Thr | Gly | His | Ser | Leu | Gly | Gly | Ala | Thr | Ala |
|     |     | 210 |     |     |     |     | 215 |     |     |     |     | 220 |     |     |     |
| Val | Leu | Ser | Ala | Leu | Asp | Leu | Tyr | His | His | Gly | His | His | Asn | Ile | Glu |
| 225 |     |     |     |     | 230 |     |     |     |     | 235 |     |     |     |     | 240 |
| Ile | Tyr | Thr | Gln | Gly | Gln | Pro | Arg | Val | Gly | Thr | Pro | Ala | Phe | Ala | Asn |
|     |     |     |     | 245 |     |     |     |     | 250 |     |     |     |     | 255 |     |
| Tyr | Val | Ile | Gly | Thr | Lys | Ile | Pro | Tyr | Gln | Arg | Leu | Val | Asn | Glu | Arg |
|     |     |     | 260 |     |     |     |     | 265 |     |     |     |     | 270 |     |     |
| Asp | Ile | Val | Pro | His | Leu | Pro | Pro | Gly | Ala | Phe | Gly | Phe | Leu | His | Ala |
|     |     | 275 |     |     |     |     | 280 |     |     |     |     | 285 |     |     |     |
| Gly | Glu | Glu | Phe | Trp | Ile | Met | Lys | Asp | Asn | Ser | Leu | Arg | Val | Cys | Pro |
|     | 290 |     |     |     |     | 295 |     |     |     |     | 300 |     |     |     |     |
| Asn | Gly | Ile | Glu | Thr | Asp | Asp | Cys | Ser | Asn | Ser | Ile | Val | Pro | Phe | Thr |
| 305 |     |     |     |     | 310 |     |     |     |     | 315 |     |     |     |     | 320 |
| Ser | Val | Ile | Asp | His | Leu | Ser | Tyr | Leu | Asp | Met | Asn | Thr | Gly | Leu | Cys |
|     |     |     |     | 325 |     |     |     |     | 330 |     |     |     |     | 335 |     |

( 2 ) INFORMATION FOR SEQ ID NO:5:

( i ) SEQUENCE CHARACTERISTICS:
        ( A ) LENGTH: 2102 base pairs
        ( B ) TYPE: nucleic acid
        ( C ) STRANDEDNESS: single
        ( D ) TOPOLOGY: linear ( i i ) MOLECULE TYPE: Genomic DNA ( x i ) SEQUENCE DESCRIPTION: SEQ ID NO:5:

```
GAATTCTAAT ATAAGCACGC TTGCCTATAT GGTGACTATA CCGATCCCAG CATTCACAAC      60
ATGGTTTCAC TTGGCCATTG TCAATGGAAT GTTTATATTT CTTTCATTAG GTAATCGTGA     120
TTTGTGATGC ATGCAAACTT GATGTATCAC AGATTATGTC AGACAAATGT GGAGCAGCAA     180
TTAATAGCAA AGCATTCACC AAAAAAGAGC AATTACTATG CACATTGGCG TATACTACAT     240
TTTTCCCCAC GCACAAGAGA TATCTTTACA CTTTTTCCTT GTTACACGCA CTTTGAAGCC     300
ATTGACTCTC GTTGGTGCGC GAGAACGGGA TGATGATATA TCAAGAGAGT TGGGGGCAAA     360
GCGGAAGCTG ATGTGAAAAA ATTACCGATC GTCATTTGTC GTTCTTGACT CTATATAAAA     420
GTAGCTTTGA TTTTGGTCTG CCAAAGTTAC CGTATTCTTG ACAAGTGATG CATTCTCATT     480
TTGTAGTCAT ATTGCTAGCT GTATTCATCT GCACGTGCTC TGTATTGGGT GTGCCACTGC     540
AAATTGATCC ACGAGATGAC AAGAGCTATG TCCCTGAACA ATATCCTTTG AAGGTGAATG     600
GTCCTTTGCC TGAAGGTGTA AGCGTGATCC AAGGCTATTG TGAAAACTGC ACCATGTATC     660
CTGAAGAAAA TAGTGTATCG GCATTCTCAT CATCATCCAC ACAAGATTAT CGTATTGCAA     720
GCGAGGCAGA GATTAAGGCA CACACATTTT ACACAGCGTT GTCAGCCAAT GCATACTGCA     780
GAACTGTCAT TCCTGGTGGT CAATGGAGTT GTCCTCACTG TGATGTTGCA CCCAACTTGA     840
ATATTACCAA GACTTTCACC ACCTTGATCA CTGATACTAA TGTCTTGGTG GCTGTTGGCG     900
AAAATGAAAA GACCATCTAT GTAGTTTTTC GTGGTACAAG CTCAATTCGC AACGCCATTG     960
CTGTAAGTTC ACCCCTTACA AACATGACAT TTATTGCTC ATCCAGCTCA TTCTTTCTCT    1020
CAGGACATTG TTTTTGTACC AGTGAATTAT CCACCTGTTA ATGGAGCCAA AGTACACAAA    1080
GGTATGTGAT CACGTGGTGT CATTTATGTA TAAGAATGCT CAATATGCTC ATTTACTATC    1140
```

-continued

| | | | | | |
|---|---|---|---|---|---|
| TAGGATTTCT | TGATAGCTAT | AACGAAGTCC | AGGATAAACT | TGTTGCTGAA | GTCAAGGCAC | 1200
| AACTTGATCG | TCATCCAGGA | TACAAGATCG | TCGTCACTGG | GTAAATACCT | GAAAAGACAT | 1260
| GGATGGCACG | TGACTAAATC | TGTGTCATTT | GTAGACATTC | GTTGGGAGGT | GCAACAGCTG | 1320
| TTCTCAGTGC | ACTTGACCTT | TATCACCATG | GCCATGACAA | TATCGAAATC | TATACTCAAG | 1380
| GTCAGCCACG | TATAGGTACT | CCAGAATTTG | CAAACTATGT | GATTGGCACC | AAGATTCCAT | 1440
| ACCAACGTCT | TGTCAATGAG | CGTGACAGTA | AGTGTACCTT | GCACAACATG | TTCGTTTTCC | 1500
| CCCGACGTAC | TAAAGTATTG | TATAGTTGTT | CCTCACCTTC | CACCTGGTGC | ATTTGGTTTC | 1560
| CTGCATGCTG | GTGAAGAGTT | TTGGATCATG | AAAGATAGCT | CGTTGCGTAA | GTAGTGTCAT | 1620
| TGAAAAGGTT | GAAGCTATAA | TACTGACTAT | ATTGGGTAGG | CGTATGTCCA | AATGGCATTG | 1680
| AAACCGACAA | CTGCAGCAAC | TCCATTGTTC | CCTTCACTAG | TGTCATTGAT | CATTTAAGGT | 1740
| GAATAGTAGC | TTTATTCATG | TCATTCATCC | ATGTAAACTA | ACACTTGTCG | TATCTAGCTA | 1800
| TCTTGACATG | AACACTGGTC | TCTGTCTATA | GTCTTTAGTA | CCATCCACTC | CTCCTCTTTA | 1860
| ATCCCTACAG | CAGTAGTTTA | AAATAAATCA | CAAGTATACT | TTGTACAAAA | CCAATCAAAT | 1920
| GGCTTTTATT | AGATGTGAAA | AAGGATGACC | AAATGCAATT | AACGAGTTTA | GTCGAAAAGA | 1980
| CCGAAGCCCA | TATCTTCATC | AGATTCCTCA | GGCTCTTCTT | CCTTGACTTC | TTCCTTCTTG | 2040
| TCATCACCAG | CAGCAGCGGG | AGCAGCAGCA | ACAACGAAAG | CATCAGGGTT | CTCCAAGAAT | 2100
| TC | | | | | | 2102

(2) INFORMATION FOR SEQ ID NO:6:

(i) SEQUENCE CHARACTERISTICS:
        (A) LENGTH: 338 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:6:

```
Met His Ser His Phe Val Val Ile Leu Leu Ala Val Phe Ile Cys Thr
 1               5                  10                  15
Cys Ser Val Leu Gly Val Pro Leu Gln Ile Asp Pro Arg Asp Asp Lys
                20                  25                  30
Ser Tyr Val Pro Glu Gln Tyr Pro Leu Lys Val Asn Gly Pro Leu Pro
            35                  40                  45
Glu Gly Val Ser Val Ile Gln Gly Tyr Cys Glu Asn Cys Thr Met Tyr
        50                  55                  60
Pro Glu Glu Asn Ser Val Ser Ala Phe Ser Ser Ser Thr Gln Asp
65                  70                  75                  80
Tyr Arg Ile Ala Ser Glu Ala Glu Ile Lys Ala His Thr Phe Tyr Thr
                85                  90                  95
Ala Leu Ser Ala Asn Ala Tyr Cys Arg Thr Val Ile Pro Gly Gly Gln
               100                 105                 110
Trp Ser Cys Pro His Cys Asp Val Ala Pro Asn Leu Asn Ile Thr Lys
           115                 120                 125
Thr Phe Thr Thr Leu Ile Thr Asp Thr Asn Val Leu Val Ala Val Gly
       130                 135                 140
Glu Asn Glu Lys Thr Ile Tyr Val Val Phe Arg Gly Thr Ser Ser Ile
145                 150                 155                 160
Arg Asn Ala Ile Ala Asp Ile Val Phe Val Pro Val Asn Tyr Pro Pro
```

|     |     |     |     | 165 |     |     |     |     | 170 |     |     |     |     | 175 |     |
| --- | --- | --- | --- | --- | --- | --- | --- | --- | --- | --- | --- | --- | --- | --- | --- |
| Val | Asn | Gly | Ala<br>180 | Lys | Val | His | Lys | Gly<br>185 | Phe | Leu | Asp | Ser | Tyr | Asn<br>190 | Glu |
| Val | Gln | Asp<br>195 | Lys | Leu | Val | Ala<br>200 | Glu | Val | Lys | Ala | Gln<br>205 | Leu | Asp | Arg | His |
| Pro | Gly<br>210 | Tyr | Lys | Ile | Val<br>215 | Val | Thr | Gly | His | Ser | Leu<br>220 | Gly | Gly | Ala | Thr |
| Ala<br>225 | Val | Leu | Ser | Ala<br>230 | Leu | Asp | Leu | Tyr | His<br>235 | His | Gly | His | Asp | Asn | Ile<br>240 |
| Glu | Ile | Tyr | Thr | Gln<br>245 | Gly | Gln | Pro | Arg | Ile<br>250 | Gly | Thr | Pro | Glu | Phe<br>255 | Ala |
| Asn | Tyr | Val | Ile<br>260 | Gly | Thr | Lys | Ile | Pro<br>265 | Tyr | Gln | Arg | Leu | Val<br>270 | Asn | Glu |
| Arg | Asp | Ile<br>275 | Val | Pro | His | Leu | Pro<br>280 | Pro | Gly | Ala | Phe | Gly<br>285 | Phe | Leu | His |
| Ala | Gly<br>290 | Glu | Glu | Phe | Trp | Ile<br>295 | Met | Lys | Asp | Ser | Ser<br>300 | Leu | Arg | Val | Cys |
| Pro<br>305 | Asn | Gly | Ile | Glu | Thr<br>310 | Asp | Asn | Cys | Ser | Asn<br>315 | Ser | Ile | Val | Pro | Phe<br>320 |
| Thr | Ser | Val | Ile | Asp<br>325 | His | Leu | Ser | Tyr | Leu<br>330 | Asp | Met | Asn | Thr | Gly<br>335 | Leu |
| Cys | Leu |     |     |     |     |     |     |     |     |     |     |     |     |     |     |

( 2 ) INFORMATION FOR SEQ ID NO:7:

( i ) SEQUENCE CHARACTERISTICS:
        ( A ) LENGTH: 1714 base pairs
        ( B ) TYPE: nucleic acid
        ( C ) STRANDEDNESS: single
        ( D ) TOPOLOGY: linear ( i i ) MOLECULE TYPE: Genomic DNA ( x i ) SEQUENCE DESCRIPTION: SEQ ID NO:7:

```
GTACGATCAT CATTTGTCGT TCTTGGTTCT ATATAAAAGT AGCTCTGATT TTGGTCAGCC      60
AAGGTCACTG TGTTCTTGAC AAGTGATGCA TTCTCATTTT GTAGTCTTAT TGCTAGCAGT     120
ATTCATCTGC ATGTGCTCTG TATCGGGTGT GCCACTGCAA ATTGATCCAC GCGATGACAA     180
GAGCTATGTT CCTGAACAAT ATCCTTTGAA GGTGAATGGT CCTTTGCCAG AAGGTGTAAG     240
CGTGATCCAA GGCTATTGTG AAAACTGTAC CATGTATCCT GAAGAAAATA GTGTATCGGC     300
ATTCTCGTCA TCATCCACAC AAGATTATCG TATTGCAAGC GAGGCAGAGA TTAAGGCACA     360
CACATTTTAC ACAGCATTGT CAGCCAATGC ATACTGCAGA ACTGTCATTC CTGGTGGTCG     420
ATGGAGCTGT CCCCACTGTG GTGTTGCATC CAATTTGCAA ATTACCAAGA CTTTCAGCAC     480
CTTAATCACT GATACTAATG TCTTGGTGGC TGTTGGCGAA AAGGAGAAGA CCATCTATGT     540
AGTTTTTCGT GGTACAAGCT CAATTCGCAA CGCCATTGCT GTAAGTTCAC CCCTTACAAA     600
CATGACACTT TGTTGCTCAT CCGACTCATT CTTTCTTACA GGACATTGTT TTTGTACCAG     660
TGAATTATCC ACCTGTTAAT GGAGCCAAAG TACACAAAGG TATGTGATGA TGTGGTGTCA     720
TTTATATATA AGAATGCTCA ATATGCTCAT TTACTATCTA GGATTTCTTG ATAGCTATAA     780
CGAAGTCCAG GATAAACTTG TTGCTGAAGT CAAGGCACAA CTTGATCGTC ATCCAGGATA     840
CAAGATCGTC GTCACTGGGT AAATACCTGA AAAGACATGG ATGGCACGTG ACTAAATCTG     900
TGTCATTGGT AGACATTCCT TGGGAGGTGC AACAGCTGTT CTCAGTGCAC TTGACCTTTA     960
TCACCATGGC CATGCCAATA TCGAAATCTA TACTCAAGGT CAGCCACGTA TAGGTACTCC    1020
```

-continued

```
AGCATTTGCA  AACTATGTGA  TTGGCACCAA  GATTCCATAC  CAACGTCTTG  TCCATGAGCG   1080

TGACAGTAAG  TGTACCTTGC  ACGACATGTT  CGTTTTCCCC  GACGTACTAA  AGTATTGTAT   1140

AGTTGTTCCT  CACCTTCCAC  CTGGTGCATT  TGGTTTCTTG  CATGCTGGTG  AAGAGTTTTG   1200

GATCATGAAA  GATAGCTCGT  TGCGTAAGTA  GTGTCATTGA  AAAGGTTGAA  GCTATAATAC   1260

TGACTATATT  GGGTAGGCGT  ATGTCCAAAT  GGCATTGAAA  CTGACAACTG  CAGCAACTCC   1320

ATTGTTCCCT  TCACTAGTGT  CATTGACCAT  TTAAGGTGAA  TAGTAGCTTT  ATTCATGTCA   1380

TTCATCCATG  TAAACTAACA  CTTGTCGTAT  CTAGCTATCT  TGACATGAAC  ACTGGTCTCT   1440

GTTTATAATC  TTTAGTATCA  TCCACTCCTC  CTCTTTAATG  CAATACTTTT  TAAGATAAAT   1500

CACAAGTATA  CTTTGTACAA  AACCAATCAA  ATGGCTTTTA  TTAGATGTGA  AAAAGGATGA   1560

CTAAATGCAA  TTAAAGAGTT  TAGTCGAAAA  GACCGAAGCC  CATATCTTCA  TCAGATTCCT   1620

CGGCCTCTTC  TTCCTTGACT  TCTTCCTTCT  TGTCATCAGC  AGCAGCAGCG  GGAGCAGCAG   1680

CAACAACGAA  AGCATCAGGG  TTCTCCAAGA  ATTC                                 1714
```

( 2 ) INFORMATION FOR SEQ ID NO:8:

( i ) SEQUENCE CHARACTERISTICS:
        ( A ) LENGTH: 337 amino acids
        ( B ) TYPE: amino acid
        ( C ) STRANDEDNESS: single
        ( D ) TOPOLOGY: linear ( i i ) MOLECULE TYPE: protein ( v ) FRAGMENT TYPE: internal ( x i ) SEQUENCE DESCRIPTION: SEQ ID NO:8:

```
Met  His  Ser  His  Phe  Val  Val  Leu  Leu  Leu  Ala  Val  Phe  Ile  Cys  Met
 1                    5                        10                       15

Cys  Ser  Val  Ser  Gly  Val  Pro  Leu  Gln  Ile  Asp  Pro  Arg  Asp  Asp  Lys
               20                       25                       30

Ser  Tyr  Val  Pro  Glu  Gln  Tyr  Pro  Leu  Lys  Val  Asn  Gly  Pro  Leu  Pro
          35                       40                       45

Glu  Gly  Val  Ser  Val  Ile  Gln  Gly  Tyr  Cys  Glu  Asn  Cys  Thr  Met  Tyr
     50                       55                       60

Pro  Glu  Glu  Asn  Ser  Val  Ser  Ala  Phe  Ser  Ser  Ser  Thr  Gln  Asp
65                       70                       75                       80

Tyr  Arg  Ile  Ala  Ser  Glu  Ala  Glu  Ile  Lys  Ala  His  Thr  Phe  Tyr  Thr
                    85                       90                       95

Ala  Leu  Ser  Ala  Asn  Ala  Tyr  Cys  Arg  Thr  Val  Ile  Pro  Gly  Gly  Arg
               100                      105                      110

Trp  Ser  Cys  Pro  His  Cys  Gly  Val  Ala  Ser  Asn  Leu  Gln  Ile  Thr  Lys
          115                      120                      125

Thr  Phe  Ser  Thr  Leu  Ile  Thr  Asp  Thr  Asn  Val  Leu  Val  Ala  Val  Gly
     130                      135                      140

Glu  Lys  Glu  Lys  Thr  Ile  Tyr  Val  Val  Phe  Arg  Gly  Thr  Ser  Ser  Ile
145                      150                      155                      160

Arg  Asn  Ala  Ile  Ala  Asp  Ile  Val  Phe  Val  Pro  Val  Asn  Tyr  Pro  Pro
                    165                      170                      175

Val  Asn  Gly  Ala  Lys  Val  His  Lys  Gly  Phe  Leu  Asp  Ser  Tyr  Asn  Glu
               180                      185                      190

Val  Gln  Asp  Lys  Leu  Val  Ala  Glu  Val  Lys  Ala  Gln  Leu  Asp  Arg  His
          195                      200                      205

Pro  Gly  Tyr  Lys  Ile  Val  Val  Thr  Gly  His  Ser  Leu  Gly  Gly  Ala  Thr
```

```
        210                          215                          220
Ala  Val  Leu  Ser  Ala  Leu  Asp  Leu  Tyr  His  His  Gly  His  Ala  Asn  Ile
225                      230                     235                          240

Glu  Ile  Tyr  Thr  Gln  Gly  Gln  Pro  Arg  Ile  Gly  Thr  Pro  Ala  Phe  Ala
                    245                      250                     255

Asn  Tyr  Val  Ile  Gly  Thr  Lys  Ile  Pro  Tyr  Gln  Arg  Leu  Val  His  Glu
               260                      265                     270

Arg  Asp  Ile  Val  Pro  His  Leu  Pro  Pro  Gly  Ala  Phe  Gly  Phe  Leu  His
          275                     280                     285

Ala  Gly  Glu  Glu  Phe  Trp  Ile  Met  Lys  Asp  Ser  Ser  Leu  Arg  Val  Cys
     290                     295                     300

Pro  Asn  Gly  Ile  Glu  Thr  Asp  Asn  Cys  Ser  Asn  Ser  Ile  Val  Pro  Phe
305                      310                     315                          320

Thr  Ser  Val  Ile  Asp  His  Leu  Ser  Tyr  Leu  Asp  Met  Asn  Thr  Gly  Leu
               325                      330                     335

Cys
```

( 2 ) INFORMATION FOR SEQ ID NO:9:

( i ) SEQUENCE CHARACTERISTICS:
        ( A ) LENGTH: 1115 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:9:

```
AAAGGCATTC  TCATTTTGTA  GTCTTATTGC  TAGCAGTATT  CATCTGCATG  TGCTCTGTAT      60
CGGGTGTGCC  ACTGCAAATT  GATCCACGCG  ATGACAAGAG  CTATGTTCCT  GAACAATATC     120
CTTTGAAGGT  GAATGGTCCT  TTGCCAGAAG  GTGTAAGCGT  GATCCAAGGC  TATTGTGAAA     180
ACTGTACCAT  GTATCCTGAA  AAAAATAGTG  TATCGGCATT  CTCGTCATCA  TCCACACAAG     240
ATTATCGTAT  TGCAAGCGAG  GCAGAGATTA  AGGCACACAC  ATTTTACACA  GCATTGTCAG     300
CCAATGCATA  CTGCAGAACT  GTCATTCCTG  GTGGTCGATG  GAGCTGTCCC  CACTGTGGTG     360
TTGCATCCAA  TTTGCAAATT  ACCAAGACTT  TCAGCACCTT  AATCACTGAT  ACTAATGTCT     420
TGGTGGCTGT  TGGCGAAAAG  GAGAAGACCA  TCTATGTAGT  TTTTCGTGGT  ACAAGCTCAA     480
TTCGCAACGC  CATTGCTGAC  ATTGTTTTTG  TACCAGTGAA  TTATCCACCT  GTTAATGGAG     540
CCAAAGTACA  CAAAGGATTT  CTTGATAGCT  ATAACGAAGT  CCAGGATAAA  CTTGTTGCTG     600
AAGTCAAGGC  ACAACTTGAT  CGTCATCCAG  GATACAAGAT  CGTCGTCACT  GGACATTCCT     660
TGGGAGGTGC  AACAGCTGTT  CTCAGTGCAC  TTGACCTTTA  TCACCATGGC  CATGCCAATA     720
TCGAAATCTA  TACTCAAGGT  CAGCCACGTA  TAGGTACTCC  AGCATTTGCA  AACTATGTGA     780
TAGGCACCAA  GATTCCATAC  CAACGTCTTG  TCCATGAGCG  TGACATTGTT  CCTCACCTTC     840
CACCTGGTGC  ATTTGGTTTC  TTGCATGCTG  GTGAAGAGTT  TTGGATCATG  AAAGATAGCT     900
CGTTGCGCGT  ATGTCCAAAT  GGCATTGAAA  CTGACAACTG  CAGCAACTCC  ATTGTTCCCT     960
TCACTAGTGT  CATTGACCAT  TTAAGCTATC  TTGACATGAA  CACTGGTCTC  TGTTTATAAT    1020
CTTTAGTATC  ATCCACTCCT  CCTCTTTAAT  GCAATACTTT  TTAAGATAAA  TCACAAGTAT    1080
ACTTTGTACA  AAACCAAAAA  AAAAAAAAA   AAAAA                                 1115
```

( 2 ) INFORMATION FOR SEQ ID NO:10:

( i ) SEQUENCE CHARACTERISTICS:

(A) LENGTH: 338 amino acids
(B) TYPE: amino acid
(C) STRANDEDNESS: single
(D) TOPOLOGY: linear (xi) SEQUENCE DESCRIPTION: SEQ ID NO:10:

```
Arg  His  Ser  His  Phe  Val  Val  Leu  Leu  Leu  Ala  Val  Phe  Ile  Cys  Met
 1              5                        10                       15

Cys  Ser  Val  Ser  Gly  Val  Pro  Leu  Gln  Ile  Asp  Pro  Arg  Asp  Asp  Lys
              20                        25                       30

Ser  Tyr  Val  Pro  Glu  Gln  Tyr  Pro  Leu  Lys  Val  Asn  Gly  Pro  Leu  Pro
              35                        40                  45

Glu  Gly  Val  Ser  Val  Ile  Gln  Gly  Tyr  Cys  Glu  Asn  Cys  Thr  Met  Tyr
         50                        55                  60

Pro  Glu  Lys  Asn  Ser  Val  Ser  Ala  Phe  Ser  Ser  Ser  Thr  Gln  Asp
65                       70                  75                            80

Tyr  Arg  Ile  Ala  Ser  Glu  Ala  Glu  Ile  Lys  Ala  His  Thr  Phe  Tyr  Thr
                   85                        90                            95

Ala  Leu  Ser  Ala  Asn  Ala  Tyr  Cys  Arg  Thr  Val  Ile  Pro  Gly  Gly  Arg
              100                      105                      110

Trp  Ser  Cys  Pro  His  Cys  Gly  Val  Ala  Ser  Asn  Leu  Gln  Ile  Thr  Lys
         115                      120                       125

Thr  Phe  Ser  Thr  Leu  Ile  Thr  Asp  Thr  Asn  Val  Leu  Val  Ala  Val  Gly
     130                      135                 140

Glu  Lys  Glu  Lys  Thr  Ile  Tyr  Val  Val  Phe  Arg  Gly  Thr  Ser  Ser  Ile
145                           150                 155                      160

Arg  Asn  Ala  Ile  Ala  Asp  Ile  Val  Phe  Val  Pro  Val  Asn  Tyr  Pro  Pro
                   165                      170                      175

Val  Asn  Gly  Ala  Lys  Val  His  Lys  Gly  Phe  Leu  Asp  Ser  Tyr  Asn  Glu
              180                      185                      190

Val  Gln  Asp  Lys  Leu  Val  Ala  Glu  Val  Lys  Ala  Gln  Leu  Asp  Arg  His
              195                      200                      205

Pro  Gly  Tyr  Lys  Ile  Val  Val  Thr  Gly  His  Ser  Leu  Gly  Gly  Ala  Thr
     210                           215                 220

Ala  Val  Leu  Ser  Ala  Leu  Asp  Leu  Tyr  His  His  Gly  His  Ala  Asn  Ile
225                      230                 235                           240

Glu  Ile  Tyr  Thr  Gln  Gly  Gln  Pro  Arg  Ile  Gly  Thr  Pro  Ala  Phe  Ala
                   245                      250                      255

Asn  Tyr  Val  Ile  Gly  Thr  Lys  Ile  Pro  Tyr  Gln  Arg  Leu  Val  His  Glu
              260                      265                      270

Arg  Asp  Ile  Val  Pro  His  Leu  Pro  Pro  Gly  Ala  Phe  Gly  Phe  Leu  His
         275                      280                      285

Ala  Gly  Glu  Glu  Phe  Trp  Ile  Met  Lys  Asp  Ser  Ser  Leu  Arg  Val  Cys
     290                      295                 300

Pro  Asn  Gly  Ile  Glu  Thr  Asp  Asn  Cys  Ser  Asn  Ser  Ile  Val  Pro  Phe
305                      310                 315                           320

Thr  Ser  Val  Ile  Asp  His  Leu  Ser  Tyr  Leu  Asp  Met  Asn  Thr  Gly  Leu
                   325                      330                      335

Cys  Leu
```

(2) INFORMATION FOR SEQ ID NO:11:

(i) SEQUENCE CHARACTERISTICS:
(A) LENGTH: 9 amino acids
(B) TYPE: amino acid
(C) STRANDEDNESS: single
(D) TOPOLOGY: linear ( x i ) SEQUENCE DESCRIPTION: SEQ ID NO:11:

| Glu | Thr | Glu | Ile | Gln | Ala | His | Thr | Phe |
|-----|-----|-----|-----|-----|-----|-----|-----|-----|
| 1   |     |     |     | 5   |     |     |     |     |

( 2 ) INFORMATION FOR SEQ ID NO:12:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:12:

GARACGARAT HCARGCCAYA CTT    23

( 2 ) INFORMATION FOR SEQ ID NO:13:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( x i ) SEQUENCE DESCRIPTION: SEQ ID NO:13:

| Pro | Pro | Gly | Ala | Phe | Gly | Phe | Leu |
|-----|-----|-----|-----|-----|-----|-----|-----|
| 1   |     |     |     | 5   |     |     |     |

( 2 ) INFORMATION FOR SEQ ID NO:14:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:14:

ARRAANCCRA AGCNCCGGNG G    21

( 2 ) INFORMATION FOR SEQ ID NO:15:

( i ) SEQUENCE CHARACTERISTICS:
        ( A ) LENGTH: 363 amino acids
        ( B ) TYPE: amino acid
        ( C ) STRANDEDNESS: single
        ( D ) TOPOLOGY: linear ( x i ) SEQUENCE DESCRIPTION: SEQ ID NO:15:

| Met | Val | Leu | Lys | Gln | Arg | Ala | Asn | Tyr | Leu | Gly | Phe | Leu | Ile | Val | Phe |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Phe | Thr | Ala | Phe | Leu | Val | Glu | Ala | Val | Pro | Ile | Lys | Arg | Gln | Ser | Asn |
|     |     |     | 20  |     |     |     |     | 25  |     |     |     |     | 30  |     |     |
| Ser | Thr | Val | Asp | Ser | Leu | Pro | Pro | Leu | Ile | Pro | Ser | Arg | Thr | Ser | Ala |
|     |     |     | 35  |     |     |     |     | 40  |     |     |     |     | 45  |     |     |
| Pro | Ser | Ser | Ser | Pro | Ser | Thr | Thr | Asp | Pro | Glu | Ala | Pro | Ala | Met | Ser |
|     |     | 50  |     |     |     |     | 55  |     |     |     |     | 60  |     |     |     |
| Arg | Asn | Gly | Pro | Leu | Pro | Ser | Asp | Val | Glu | Thr | Lys | Tyr | Gly | Met | Ala |
| 65  |     |     |     |     | 70  |     |     |     |     | 75  |     |     |     |     | 80  |
| Leu | Asn | Ala | Thr | Ser | Tyr | Pro | Asp | Ser | Val | Val | Gln | Ala | Met | Ser | Ile |
|     |     |     |     | 85  |     |     |     |     | 90  |     |     |     |     | 95  |     |
| Asp | Gly | Gly | Ile | Arg | Ala | Ala | Thr | Ser | Gln | Glu | Ile | Asn | Glu | Leu | Thr |
|     |     |     | 100 |     |     |     |     | 105 |     |     |     |     | 110 |     |     |
| Tyr | Tyr | Thr | Thr | Leu | Ser | Ala | Asn | Ser | Tyr | Cys | Arg | Thr | Val | Ile | Pro |
|     |     |     | 115 |     |     |     |     | 120 |     |     |     |     | 125 |     |     |

Gly Ala Thr Trp Asp Cys Ile His Cys Asp Ala Thr Glu Asp Leu Lys
130             135             140

Ile Ile Lys Thr Trp Ser Thr Leu Ile Tyr Asp Thr Asn Ala Met Val
145             150             155             160

Ala Arg Gly Asp Ser Glu Lys Thr Ile Tyr Ile Val Phe Arg Gly Ser
        165             170             175

Ser Ser Ile Arg Asn Trp Ile Ala Asp Leu Thr Phe Val Pro Val Ser
        180             185             190

Tyr Pro Pro Val Ser Gly Thr Lys Val His Lys Gly Phe Leu Asp Ser
    195             200             205

Tyr Gly Glu Val Gln Asn Glu Leu Val Ala Thr Val Leu Asp Gln Phe
    210             215             220

Lys Gln Tyr Pro Ser Tyr Lys Val Ala Val Thr Gly His Ser Leu Gly
225             230             235             240

Gly Ala Thr Ala Leu Leu Cys Ala Leu Asp Leu Tyr Gln Arg Glu Glu
            245             250             255

Gly Leu Ser Ser Ser Asn Leu Phe Leu Tyr Thr Gln Gly Gln Pro Arg
            260             265             270

Val Gly Asp Pro Ala Phe Ala Asn Tyr Val Val Ser Thr Gly Ile Pro
        275             280             285

Tyr Arg Arg Thr Val Asn Glu Arg Asp Ile Val Pro His Leu Pro Pro
    290             295             300

Ala Ala Phe Gly Phe Leu His Ala Gly Glu Glu Tyr Trp Ile Thr Asp
305             310             315             320

Asn Ser Pro Glu Thr Val Gln Val Cys Thr Ser Asp Leu Glu Thr Ser
            325             330             335

Asp Cys Ser Asn Ser Ile Val Pro Phe Thr Ser Val Leu Asp His Leu
            340             345             350

Ser Tyr Phe Gly Ile Asn Thr Gly Leu Cys Thr
        355             360

( 2 ) INFORMATION FOR SEQ ID NO:16:

( i ) SEQUENCE CHARACTERISTICS:
        ( A ) LENGTH: 291 amino acids
        ( B ) TYPE: amino acid
        ( C ) STRANDEDNESS: single
        ( D ) TOPOLOGY: linear ( x i ) SEQUENCE DESCRIPTION: SEQ ID NO:16:

Met Arg Ser Ser Leu Val Leu Phe Phe Val Ser Ala Trp Thr Ala Leu
1               5               10              15

Ala Ser Pro Ile Arg Arg Glu Val Ser Gln Asp Leu Phe Asn Gln Phe
        20              25              30

Asn Leu Phe Ala Gln Tyr Ser Ala Ala Ala Tyr Cys Gly Lys Asn Asn
        35              40              45

Asp Ala Pro Ala Gly Thr Asn Ile Thr Cys Thr Gly Asn Ala Cys Pro
    50              55              60

Glu Val Glu Lys Ala Asp Ala Thr Phe Leu Tyr Ser Phe Glu Asp Ser
65              70              75              80

Gly Val Gly Asp Val Thr Gly Phe Leu Ala Leu Asp Asn Thr Asn Lys
        85              90              95

Leu Ile Val Leu Ser Phe Arg Gly Ser Arg Ser Ile Glu Asn Trp Ile
            100             105             110

Gly Asn Leu Asn Phe Asp Leu Lys Glu Ile Asn Asp Ile Cys Ser Gly
        115             120             125

| | | | | | | | | | | | | | | |
|---|---|---|---|---|---|---|---|---|---|---|---|---|---|---|
| Cys | Arg 130 | Gly | His | Asp | Gly | Phe 135 | Thr | Ser | Ser | Trp | Arg 140 | Ser | Val | Ala | Asp |
| Thr 145 | Leu | Arg | Gln | Lys | Val 150 | Glu | Asp | Ala | Val | Arg 155 | Glu | His | Pro | Asp | Tyr 160 |
| Arg | Val | Val | Phe | Thr 165 | Gly | His | Ser | Leu | Gly 170 | Gly | Ala | Leu | Ala | Thr 175 | Val |
| Ala | Gly | Ala | Asp 180 | Leu | Arg | Gly | Asn | Gly 185 | Tyr | Asp | Ile | Asp | Val 190 | Phe | Ser |
| Tyr | Gly | Ala 195 | Pro | Arg | Val | Gly | Asn 200 | Arg | Ala | Phe | Ala | Glu 205 | Phe | Leu | Thr |
| Val | Gln 210 | Thr | Gly | Gly | Thr | Leu 215 | Tyr | Arg | Ile | Thr | His 220 | Thr | Asn | Asp | Ile |
| Val 225 | Pro | Arg | Leu | Pro | Pro 230 | Arg | Glu | Phe | Gly | Tyr 235 | Ser | His | Ser | Ser | Pro 240 |
| Glu | Tyr | Trp | Ile | Lys 245 | Ser | Gly | Thr | Leu | Val 250 | Pro | Val | Thr | Arg | Asn 255 | Asp |
| Ile | Val | Lys | Ile 260 | Glu | Gly | Ile | Asp | Ala 265 | Thr | Gly | Gly | Asn | Asn 270 | Gln | Pro |
| Asn | Ile | Pro 275 | Asp | Ile | Pro | Ala | His 280 | Leu | Trp | Tyr | Phe | Gly 285 | Leu | Ile | Gly |
| Thr | Cys 290 | Leu | | | | | | | | | | | | | |